(12) United States Patent
Prestrelski et al.

(10) Patent No.: US 11,020,403 B2
(45) Date of Patent: Jun. 1, 2021

(54) PRECIPITATION RESISTANT SMALL MOLECULE DRUG FORMULATIONS

(71) Applicant: XERIS PHARMACEUTICALS, INC., Chicago, IL (US)

(72) Inventors: Steven J. Prestrelski, San Diego, CA (US); Michael A. Sandoval, Beaverton, OR (US); Brian R. Sloat, Austin, TX (US)

(73) Assignee: Xeris Pharmaceuticals, Inc., Chicago, IL (US)

( * ) Notice: Subject to any disclaimer, the term of this patent is extended or adjusted under 35 U.S.C. 154(b) by 0 days.

(21) Appl. No.: 15/994,832

(22) Filed: May 31, 2018

(65) Prior Publication Data

US 2018/0369255 A1 Dec. 27, 2018

Related U.S. Application Data

(60) Provisional application No. 62/514,474, filed on Jun. 2, 2017.

(51) Int. Cl.
| | | |
|---|---|---|
| *A61K 31/5513* | (2006.01) | |
| *A61K 9/00* | (2006.01) | |
| *A61K 9/08* | (2006.01) | |
| *A61K 47/20* | (2006.01) | |
| *A61K 47/22* | (2006.01) | |
| *A61K 47/14* | (2017.01) | |
| *A61K 47/16* | (2006.01) | |
| *A61K 47/26* | (2006.01) | |
| *A61K 47/28* | (2006.01) | |
| *A61P 25/08* | (2006.01) | |
| *A61P 25/14* | (2006.01) | |
| *A61P 25/22* | (2006.01) | |

(52) U.S. Cl.
CPC ........ *A61K 31/5513* (2013.01); *A61K 9/0019* (2013.01); *A61K 9/08* (2013.01); *A61K 47/14* (2013.01); *A61K 47/16* (2013.01); *A61K 47/20* (2013.01); *A61K 47/22* (2013.01); *A61K 47/26* (2013.01); *A61K 47/28* (2013.01); *A61P 25/08* (2018.01); *A61P 25/14* (2018.01); *A61P 25/22* (2018.01)

(58) Field of Classification Search
CPC .... A61K 31/5513; A61K 9/0019; A61K 9/08; A61K 47/14; A61K 47/16; A61K 47/20; A61K 47/22; A61K 47/26; A61K 47/28; A61P 25/08; A61P 25/14; A61P 25/22
See application file for complete search history.

(56) References Cited

U.S. PATENT DOCUMENTS

| | | |
|---|---|---|
| 3,016,895 A | 1/1962 | Sein |
| 4,272,548 A * | 6/1981 | Gatzen .................. A61K 31/23 514/547 |
| 4,608,764 A | 9/1986 | Leuenberger |
| 4,848,094 A | 7/1989 | Davis et al. |
| 4,927,571 A | 5/1990 | Huang et al. |
| 5,031,336 A | 7/1991 | Diesner et al. |
| 5,092,843 A | 3/1992 | Monroe et al. |
| 5,208,998 A | 5/1993 | Oyler |
| 5,260,306 A | 11/1993 | Boardman et al. |
| 5,397,771 A | 3/1995 | Bechgaard et al. |
| 5,716,640 A | 2/1998 | Kamei et al. |
| 5,932,547 A | 8/1999 | Stevenson et al. |
| 5,977,082 A | 11/1999 | Gatti et al. |
| 6,001,336 A | 12/1999 | Gordon |
| 6,051,256 A | 4/2000 | Platz et al. |
| 6,124,261 A | 9/2000 | Stevenson et al. |
| 6,199,297 B1 | 3/2001 | Wisniewski |
| 6,253,463 B1 | 7/2001 | Hansen |
| 6,264,990 B1 | 7/2001 | Knepp et al. |
| 6,290,991 B1 | 9/2001 | Roser et al. |
| 6,309,663 B1 | 10/2001 | Patel et al. |
| 6,331,310 B1 | 12/2001 | Roser et al. |
| 6,365,637 B1 | 4/2002 | Zirnstein et al. |
| 6,371,939 B2 | 4/2002 | Bergens et al. |
| 6,495,164 B1 | 12/2002 | Ramstack et al. |
| 6,667,061 B2 | 12/2003 | Ramstack et al. |
| 6,676,958 B2 | 1/2004 | Gerber |
| 6,730,328 B2 | 5/2004 | Maskiewicz et al. |
| 7,005,421 B2 | 2/2006 | Gatti et al. |

(Continued)

FOREIGN PATENT DOCUMENTS

| | | |
|---|---|---|
| CN | 1507858 | 6/2004 |
| CN | 1582170 | 2/2005 |

(Continued)

OTHER PUBLICATIONS

Rosoff et. al., International Journal of Pharmaceutics, 1980, Elsevier/North Holland Biomedical Press, vol. 6, pp. 137-146 (Year: 1980).*

Office Action issued in Indian Patent Application No. 10985/DELNP/2014, dated Aug. 17, 2018 and received Sep. 23, 2018.

Office Action issued in Israeli Patent Application No. 236393, dated Nov. 12, 2018.

Administer Intramuscular, Subcutaneous, and Intradermal Injections, from http://www.brooksidepress.org/Products/Administer_IM_SQ_and_ID_Injections/lesson_1 . . . , pp. 1-3, published on 2007.

Amylin Agonists, from http://www.globalrph.com/amylin-agonists.htm, pp. 1-5, accessed Nov. 30, 2014.

(Continued)

*Primary Examiner* — Sarah Pihonak
(74) *Attorney, Agent, or Firm* — Sterne, Kessler, Goldstein & Fox P.L.L.C.

(57) ABSTRACT

Embodiments of the invention are directed to formulations that provide a solution to the problem of small molecule (e.g., diazepam) precipitation at the injection site when administered as a highly-concentrated formulation. In certain aspects the formulations include at least one surfactant in a non-aqueous formulation, which prevents small molecule precipitation and improves the bioavailability of the drug by enhancing absorption into the systemic circulation.

22 Claims, 3 Drawing Sheets

(56) References Cited

U.S. PATENT DOCUMENTS

| | | |
|---|---|---|
| 7,163,704 B2 | 1/2007 | Zhang |
| 7,259,225 B2 | 8/2007 | Song et al. |
| 7,314,636 B2 | 1/2008 | Caseres et al. |
| 7,371,406 B2 | 5/2008 | Rasstack et al. |
| 7,396,841 B2 | 7/2008 | Doen et al. |
| 7,442,832 B2 | 10/2008 | Gentile et al. |
| 7,498,312 B2 | 3/2009 | Cohen et al. |
| 7,582,311 B1 | 9/2009 | Cleland et al. |
| 7,604,822 B2 | 10/2009 | Ionascu |
| 7,651,703 B2 | 1/2010 | Cleland et al. |
| 7,915,229 B2 | 3/2011 | Cohen et al. |
| 8,110,209 B2 | 2/2012 | Prestrelski et al. |
| 8,946,208 B2 | 2/2015 | Castile et al. |
| 9,125,805 B2 | 9/2015 | Prestrelski et al. |
| 9,138,479 B2 | 9/2015 | Prestrelski et al. |
| 2002/0179647 A1 | 12/2002 | Hall et al. |
| 2003/0013753 A1 | 1/2003 | Aung-Din |
| 2003/0026884 A1 | 2/2003 | Mantius et al. |
| 2003/0119825 A1 | 6/2003 | Folger et al. |
| 2003/0170289 A1 | 9/2003 | Chen et al. |
| 2003/0191157 A1 | 10/2003 | Doen et al. |
| 2004/0142043 A1 | 7/2004 | Maeda et al. |
| 2004/0176341 A1 | 9/2004 | Chou et al. |
| 2005/0019436 A1 | 1/2005 | Burch et al. |
| 2005/0069591 A1 | 3/2005 | Bernstein et al. |
| 2005/0240166 A1 | 10/2005 | Harper et al. |
| 2006/0160823 A1 | 7/2006 | Witchey-Lakshmanan et al. |
| 2006/0211982 A1 | 9/2006 | Prestrelski et al. |
| 2007/0196416 A1 | 8/2007 | Li et al. |
| 2008/0096967 A1 | 4/2008 | Lopez et al. |
| 2008/0132493 A1 | 6/2008 | Folger et al. |
| 2008/0145383 A1 | 6/2008 | Zauner et al. |
| 2008/0160067 A1 | 7/2008 | Boeckh et al. |
| 2008/0200383 A1 | 8/2008 | Lassner et al. |
| 2008/0220069 A1 | 9/2008 | Allison |
| 2008/0226689 A1 | 9/2008 | Berry et al. |
| 2008/0248999 A1 | 10/2008 | Steiner |
| 2008/0260840 A1 | 10/2008 | Alessi et al. |
| 2008/0305161 A1 | 12/2008 | Shah et al. |
| 2009/0143737 A1 | 6/2009 | Kobayashi et al. |
| 2009/0215883 A1 | 8/2009 | Bouzada et al. |
| 2009/0226530 A1 | 9/2009 | Jennings et al. |
| 2009/0233912 A1 | 9/2009 | Castile et al. |
| 2010/0098735 A1 | 4/2010 | Jain et al. |
| 2010/0120660 A1 | 5/2010 | Balschmidt et al. |
| 2011/0223208 A1 | 9/2011 | Hill et al. |
| 2011/0230569 A1 | 9/2011 | Nistor et al. |
| 2012/0046225 A1 | 2/2012 | Prestrelski et al. |
| 2012/0232001 A1 | 9/2012 | Prestrelski et al. |
| 2013/0065886 A1* | 3/2013 | Cartt ............... A61K 9/0043 514/221 |
| 2013/0123739 A1 | 5/2013 | Yoshikawa |
| 2013/0317477 A1 | 11/2013 | Edwards et al. |
| 2014/0005135 A1* | 1/2014 | Prestrelski ............ A61K 9/08 514/40 |
| 2014/0058337 A1 | 2/2014 | Claussen et al. |
| 2014/0128381 A1* | 5/2014 | Bream ............... A61P 25/00 514/221 |
| 2014/0171362 A1 | 6/2014 | Prestrelski et al. |
| 2014/0179599 A1 | 6/2014 | Prestrelski et al. |
| 2014/0179600 A1 | 6/2014 | Prestrelski et al. |
| 2014/0221288 A1 | 8/2014 | Prestrelski et al. |
| 2014/0296191 A1* | 10/2014 | Patel ................ A61K 47/10 514/167 |
| 2015/0250855 A1 | 9/2015 | Prestrelski et al. |
| 2016/0000702 A1* | 1/2016 | Schwarz ............ A61K 9/1075 514/221 |
| 2016/0000803 A1* | 1/2016 | Schwarz ............ A61K 9/006 514/221 |
| 2017/0007675 A1 | 1/2017 | Prestrelski et al. |
| 2017/0049858 A1 | 2/2017 | Prestrelski et al. |

FOREIGN PATENT DOCUMENTS

| | | |
|---|---|---|
| CN | 101842079 | 9/2010 |
| CN | 102164579 | 8/2011 |
| EP | 0916347 | 5/1999 |
| EP | 1502589 | 2/2005 |
| EP | 2030610 | 3/2009 |
| EP | 2060268 | 5/2009 |
| EP | 2526996 | 11/2012 |
| GB | 2 119 248 | 11/1983 |
| JP | H05-507085 | 10/1993 |
| JP | H07-506287 | 7/1995 |
| JP | 2006-506363 | 2/2006 |
| JP | 2006-511582 | 4/2006 |
| JP | 2007-537283 | 12/2007 |
| JP | 2008-543857 | 12/2008 |
| JP | 2009-523798 | 6/2009 |
| JP | 2010-537963 | 12/2010 |
| JP | 2011-520875 | 7/2011 |
| JP | 2014-507484 | 3/2014 |
| JP | 2014-510077 | 4/2014 |
| WO | WO 2016/022831 | 2/1916 |
| WO | WO 2016/196976 | 12/1916 |
| WO | WO 1991/16882 | 11/1991 |
| WO | WO 1994/013344 | 6/1994 |
| WO | WO 1995/32730 | 12/1995 |
| WO | WO 1996/009814 | 4/1996 |
| WO | WO 1998/009613 | 3/1998 |
| WO | WO 1998/016250 | 4/1998 |
| WO | WO 1998/027963 | 7/1998 |
| WO | WO 2000/016829 | 3/2000 |
| WO | WO 2001/076682 | 10/2001 |
| WO | WO 2001/078687 | 10/2001 |
| WO | WO 2002/000137 | 1/2002 |
| WO | WO 2002/049660 | 6/2002 |
| WO | WO 2003/007782 | 1/2003 |
| WO | WO 2003/041684 | 5/2003 |
| WO | WO 2003/051398 | 6/2003 |
| WO | WO03051398 | 6/2003 |
| WO | WO 2004/035601 | 4/2004 |
| WO | WO 2004/037242 | 5/2004 |
| WO | WO 2004/057939 | 7/2004 |
| WO | WO 2004/057959 | 7/2004 |
| WO | WO 2004/091666 | 10/2004 |
| WO | WO 2004/098643 | 11/2004 |
| WO | WO 2005/112893 | 1/2005 |
| WO | WO 2005/010079 | 2/2005 |
| WO | WO 2005/021046 | 3/2005 |
| WO | WO 2006/031376 | 3/2006 |
| WO | WO 2006/110551 | 10/2006 |
| WO | WO 2006/122217 | 11/2006 |
| WO | WO 2006/138347 | 12/2006 |
| WO | WO 2007/059019 | 5/2007 |
| WO | WO 2007/140312 | 12/2007 |
| WO | WO 2008/030469 | 3/2008 |
| WO | WO 2008/041245 | 4/2008 |
| WO | WO 2008/098212 | 8/2008 |
| WO | WO 2008/132224 | 11/2008 |
| WO | WO 2009/027697 | 3/2009 |
| WO | WO 2009/045837 | 4/2009 |
| WO | WO 2009/060473 | 5/2009 |
| WO | WO 2009/070298 | 6/2009 |
| WO | WO 2010/018596 | 2/2010 |
| WO | WO 2010/024209 | 3/2010 |
| WO | WO 2010/036702 | 4/2010 |
| WO | WO 2011/060908 | 5/2011 |
| WO | WO 2011/154725 | 12/2011 |
| WO | WO2011154725 | 12/2011 |
| WO | WO 2012/012460 | 1/2012 |
| WO | WO 2012/122535 | 9/2012 |
| WO | WO 2013/067022 | 5/2013 |
| WO | WO 2013/173687 | 11/2013 |
| WO | WO 2014/004895 | 1/2014 |
| WO | WO 2014/036323 | 3/2014 |
| WO | WO 2014/124151 | 8/2014 |
| WO | WO 2015/120231 | 8/2015 |

(56) References Cited

FOREIGN PATENT DOCUMENTS

| WO | WO 2015/153728 | 10/2015 |
|----|----------------|---------|
| WO | WO 2016/201248 | 12/2016 |

OTHER PUBLICATIONS

Anderson et al., "Revised estimate of the prevalence of multiple sclerosis in the United States", Ann. Neruol, 31(3):333-336, 1992.
Amon and Aharoni, "Neurogenesis and neuroprotection in the CNS—fundamental elements in the effect of Glatiramer acetate on treatment of autoimmune neurological disorders", Mol. Neurobiol., 36:245-253, 2007.
Autret, E. et al.: "Double-blind, randomized trial of diazepam versus placebo for prevention of recurrence of febrile seizures", The Journal of Pediatrics, vol. 117, No. 3, Sep. 1990, p. 490-494.
Bjartmar and Fox, "Pathological mechanisms and disease progression of multiple sclerosis: therapeutic implications", Drugs of Today, 38:17-29, 2002.
Bornstein et al., "A pilot trial of Cop 1 in exacerbateing remitting multiple sclerosis", New Eng. J. Med., 317:408-414,1987.
Bornstein et al., "A placebo-controlled, double-blind, randomized, two-center, pilot trial of Cop-1 in chronic progressive multiple sclerosis", Neurology, 41:533-539, 1991.
Bromberg, L. et al., "Transport of proteins dissolved in organic solvents across biomimetic membranes", Proceedings of the National Academy of Sciences 92(5):1262-1266, 1995.
Brown: "Clinicians' Guide to Diabetes Gadgets and Gizmos", Clinical Diabetes, 2008, 26, pp. 66-71.
Buffer Reference Center, from http://sigmaaldrich.com/life-science/core-bioreagents/biological-buffers/learningcenter. Accessed Jul. 3, 2013.
Carpenter, et al., "Rational Design of Stable Lyophilized Protein Formulations: Theory and Practice." pp. 1-25. 2002.
Cervera et al, "Mechanism of action of exenatide to reduce postprandial hyperglycemia in type 2 diabetes", Am. J. Physiol. Endocrinol. Metab., 294:E846-E852, 2008.
Chang and Hershenson, "Practical Approaches to Protein Formulation Development", In: Rationale Design of stable protein formulations—theory and practice, pp. 1-25, 2002.
Chang et al., "Development of a Stable Freeze-dried formulation of Recombinant Human Interleukin-1 Receptor Antagonist", Pharmaceutical Research, 13(2):243-249, 1996.
Citric Acid, from http://www.boldsky.com/health/nutrition/2011/natural-citric-acid-sources-030811.html, pp. 1-3, accessed Nov. 26, 2014.
Comi & Filippi, "Treatment with glatiramer acetate delays conversion to clinically definiate multiple sclerosis (CDMS) in patients with clinically isolated syndromes (CIS)", Neurology, 71(2):153, 2008.
Comi et al, "Results from a phase III, one-year, randomized, double-blind, parallel-group, dosecomparison study with glatiramer acetate in relapsing-remitting multiple sclerosis", Mult. Scler., 14(suppl. 1):S299, 2008.
Comi et al., "European/Canadian multicener, double-blind, randomized, placebo-controlled study of the effects of glatiramer acetate on magnetic resonance imaging-measured disease activity and burden in patents with relapsing multiple sclerosis", Ann. Neurol., 49:290-297, 2001.
Compston et al., "The Story of Multiple Sclerosis" In: McAlpine's Multiple Sclerosis. London: Churchill Livingston, pp. 3-42, 2006.
Definition of analog, from http://cancerweb.ncl.ac.uk/cgi-bin/omd?query=analog, pp. 1-5, accessed Jul. 7, 2005.
Definition of mimetic, from http://www.merriam-webster.com/medical/mimetic, p. 1, accessed Jun. 26, 2014.
DeLuca, "Freeze drying of pharmaceuticals", J. Vac. Sci. Technol., 14(1):620, 1977.
Dhib-Jalbut, "Glatirmaer acetate (Copaxone) therapy for multiple sclerosis", Pharmacol Ther., 98:245-255,, 2003.
Dhib-Jalbut, "Mechanisms of action of interferons and glatiramer acetate in multiple sclerosis", Neurology, 25 58(Suppl 4):S3-S9, 2002.
Diabetes Mellitus-Merck Manual, from http://www.merckmanuals.com/professional/print!endocrine_and_metabolic_disorders/diab . . . , pp. 1-22, accessed Apr. 2, 2013.
DMSO Facts, from http://www.theundergroundcure.com/dmso-facts.html, p. 1, accessed Nov. 26, 2014.
Encyclopedia of Pharmaceutical Technology, vol. 6, Suspensions, pp. 3597-3610, 2007.
Engeloch et al: "Stability of Screening Compounds in Wet DMSO", Journal of Biomolecular Screening, 2008, 13, pp. 999-1006.
European Search Report for EP Appl. No. EP 12180169.0 dated Oct. 25, 2012.
Fleming and Carrithers, "Diagnosis and management of multiple sclerosis", Professional communications, Inc., 4 pages, 2002.
Geary and Smith, "Pancreatic Glucagon Fails to Inhibit Sham Feeding in the Rat", Peptides, 1:163-166, 1982.
Glossary of medical education terms, institute of International Medical Education. http://www.iime.org/glossary.htm. Accessed in Mar. 2013.
Griebel et al., "SL651498, a $GABA_A$ Receptor Agonist with Subtype-Selective Efficacy, as a Potential Treatment for Generalized Anxiety Disorder and Muscle Spasms," *CNS Drug Reviews*, 2003, 9(1):3-20.
Guideline on clinical investigation of medicinal products for the treatment of multiple sclerosis EMEA, London Sep. 16, 2006.
Human insulin, from http://www.ncbi.nlm.nih.gov/protein/AAA59172. 1, p. 1, accessed Nov. 26, 2014.
Hydrochloric Acid, from http://peoplesrx.com/hyrodchloric-acid-and-bodys-primary-digestant/, pp. 1-2, accessed Jun. 23, 2016.
Hypoglycemia—Merck Manual, from http://web.archive.org/web/20120115004118/http://www.merckmanuals.com/professional/ pp. 1-2, published on May 2007.
Iasemidis LD, "Epileptic Seizure Prediction and Control." IEEE Transac Biomed Eng. 50:549-558. 2003.
International Search Report and Written Opinion issued in International Patent Application No. PCT/US2018/035473, dated Jul. 31, 2018.
International Search Report and Written Opinion issued in PCT Application PCT/US2013/048293, dated Aug. 8, 2013.
International Search Report and Written Opinion issued in PCT Application PCT/US2012/062816, dated Jan. 31, 2013.
International Search Report and Written Opinion issued in PCT Application No. PCT/US2014/015123, dated Apr. 3, 2014.
International Search Report and Written Opinion issued in PCT Application PCT/US2011/044576, dated Dec. 14, 2011.
International Search Report and Written Opinion issued in PCT Application PCT/US2012/028621, dated Aug. 22, 2012.
Johnson et al., "Extended use of glatiramer acetate (Copaxone) is well tolerated and maintains its clinical effect on multiple sclerosis relapse rate and degree of disability", Neurology, 50:701-708, 1998.
Kansara et al., "Subcutaneous delivery", Drug. Deliv. Technol, 9(6):38-42, 2009.
Knudsen "Recurrence risk after first febrile seizure and effect of short term diazepam prophylaxis," *Archives of Disease in Childhood*, 1985, 60:1045-1049.
Lzutsu, Stabilization of Therapeutic Proteins by Chemical and Physical Methods, pp. 287-292, from Therapeutic Proteins Methods and Protocols, Edited by C. Mark Smales and David C. James, published on 2005.
Meyer et al., "Preparation and in vitro characterization of gentamycin-impregnated biodegradable beads suitable for treatment of osteomyelitis ", Journal of Pharmaceutical Sciences, 87(9):1149-1154, 1998.
Naturally-occurring amino acids, from https://www.benjamin-mills.com/chemistry/amino-acids.htm pp. 1-5, accessed Jun. 23, 2016.
Noseworthy et al, "Multiple sclerosis", New Engl. J. Med., 343:938-952, 2000.
Notice of Reasons for Rejection issued in Japanese Application No. 2015-520527, dated May 10, 2017.
Pellock, John et al.: Pediatric Epilepsy: Diagnosis and Therapy: Third Edition—Chapter 19 "Febrile Seizures", 2008, p. 293-301.

(56) References Cited

OTHER PUBLICATIONS

Richards et al. "Trehalose: a review of properties, history and human tolerance and results of multiple safety studies," *Food and Chemical Toxicology* 40:871-898. 2002.
Rubino, "Solubilization of Some Poorly Soluble Drug by cosolvents", PhD dissertation, The University of Arizona, 1984.
Ruggiere et al., "Glatiramer acetate in multiple sclerosis: A review", CNS Drug Reviews, 13(2):178-191, 2007.
Shinnar et al., "Pediatric Epilepsy: Diagnosis and Therapy, Chapter 19, Febrile Seizures," 2007, 3:293-301.
Shire et al., "Challenges in the development of high protein concentration formulations", J. Pharm. Sci., 93(6):1390-1402, 2004.
Tselis et al., "Glatiramer acetate in the treatment of multiple sclerosis", Neuropsychiatric Dis. Treat. 5Q, 3(2):259-267, 2007.
Vanderweele et al., "Glucagon, Satiety From Feeding and Liver/Pancreatic Interactions," Brain Research Bulletin, 17:539-543 (1986).
Wang, "Lyophilization and development of solid protein pharmaceuticals", International Journal of Pharmaceutics, 203:1-60, 2000.
Water, from http://www.biology-online.org/dictionary/Water, pp. 1-3, accessed Apr. 24, 2014.
Weber et al., "Mechanism of action of glatiramer acetate in treatment of multiple sclerosis", Neurotherapeutics, 4(4):647-653, 2007.
Williams and Polli, "The lyophilization of pharmaceuticals: a literature review", Journal of Parenteral Science and Technology, 38(2), 1984.
Wolinsky et al, "Glatiramer acetate in primary progressive multiple sclerosis: Results of a multinationa, multicener, double-blind, placebo-controlled trial", Ann Neurool, 61:14-24, 2007.
Wolinsky, "The use of glatiramer acetate in the treatment of multiple sclerosis", Adv. Neurol., pp. 273-292, 2006.
Zacharis et al., "Volatile buffers can override the 'pH memory' of subtilisin catalysis in organic media", Proc. Natl. Acad. Sci. USA, 96:1201-1205, 1999.
Ziemssen and Schrempf, "Glatiramer acetate: Mechanisms of action in multiple sclerosis", International Rev. of Neurobiol., 79:537-570, 2007.
Crankshaw & Raper, "The Effect of Solvents on the Potency of Chlordiazepoxide, Diazepam, Medazepam, and Nitrazepam," *Journal of Pharmacy and Pharmacology*, 23(5): 313-321, 1971.
Office Action Issued in Corresponding Brazil Patent Application No. BR112014032695-9, dated Oct. 29, 2019.
Office Action Issued in Corresponding Korean Patent Application No. 1020157002262, dated Oct. 1, 2019.
Daiichi Sankyo, Heavy Metal Detoxicant Japanese Pharmacopoeia Dimercaprol Injection BAL Intramuscular Injection 100 mg "Daiichi Sankyo", $6^{th}$ edition, 2009, p. 1-2.
Edited by Katsuharu Kato, Medical English-Japanese Dictionary, B6 size, $11^{th}$ edition, $3^{rd}$ issue, Nanzando, 2002, p. 1082.
Eisai, Anesthesia Induction Agent, Sairesu intravenous push 2mg appended paper, $7^{th}$ edition, 2009, p. 1-3.
Ellson et al., In situ DMSO hydration measurements of HTS compound libraries. Comb Chem High Throughout Screen, Sep. 8, 2005, (6):489-98 (Abstract only).
Extended European Search Report issued in European Application No. 17151475.5, dated Sep. 4, 2017.

Fuji Pharma, sustained Corpus Luteum Hormone formulation PROGESTON Depot Intramuscular Injection 125 mg, $4^{th}$ edition, 2009, p. 1-2.
International Search Report and Written Opinion issued in PCT/US2015/044060, dated Nov. 2, 2015.
International Search Report and Written Opinion issued in PCT/US2015/014756, dated Sep. 25, 2015.
International Search Report and Written Opinion issued in PCT/US2015/023820, dated Jun. 18, 2015.
International Preliminary Report on Patentability and Written Opinion issued in International Patent Application No. PCT/US2016/036921, dated Dec. 12, 2017.
International Preliminary Report on Patentability issued in International Application No. PCT/US2016/035792, dated Dec. 14, 2017.
International Preliminary Report on Patentability issued in International Application No. PCT/US2016/053628, dated Jan. 3, 2018.
Nanzando, Medical Dictionary (Deluxe Version), $18^{th}$ edition, $1^{st}$ issue, Nanzando, 1998, p. 1366.
Notice of Reasons for Rejection issued in Japanese Application No. 2015-520527, dated Nov. 30, 2017.
Office Action Issued in Corresponding Chinese Patent Application No. 2017110914084, dated Jan. 19, 2020.
Office Action issued in Australian Application No. 2017200295, dated Nov. 30, 2017.
Office Action issued in European Application No. 15750582.7, dated Feb. 2, 2018.
Office Action issued in Indonesian Patent Application No. P-00201403186, dated Oct. 17, 2017.
Office Action issued in Israeli Application No. 228348, dated Oct. 29, 2017.
Office Action issued in Israeli Application No. 236393, dated Jul. 12, 2017.
Office Action issued in Thai Patent Application No. 140102311, dated Nov. 2, 2017.
Taiyo Yakuhin Kogyo, Minor Tranquilizer Diazepam Injection 10 mg "Taiyo" appended paper, $9^{th}$ edition, 2009, p. 1-2.
Written Opinion issued in International Application No. PCT/US2016/053628, dated Sep. 28, 2017.
Office Action issued in European Patent Application No. 15706976.6, dated Mar. 8, 2018.
Office Action issued in Canadian Patent Application No. 2,829,400, dated Mar. 20, 2018.
Office Action issued in Chinese Patent Application No. 201610221799.6, dated May 3, 2018.
Office Action issued in Indian Patent Application No. 3948/DELNP/2014, dated Apr. 26, 2018.
Office Action issued in United Arab Emirates Patent Application No. 960/2013, dated Mar. 12, 2018.
Office Action issued in Japanese Patent Application No. 2017-506262, dated Mar. 4, 2019.
Office Action issued in Chinese Patent Application No. 201580018099, dated Jan. 3, 2019.
Office Action issued in United Arab Emirates Application No. 1426/2014, dated Feb. 3, 2019.
Search Report Issued in Corresponding Chinese Patent Application No. 2017110914084, dated Jan. 10, 2020.

\* cited by examiner

PRECIPITATION RESISTANT SMALL MOLECULE DRUG FORMULATIONS

CROSS REFERENCE TO RELATED APPLICATIONS

This Application claims priority to U.S. Provisional Patent Application Ser. No. 62/514,474 filed Jun. 2, 2017, which is incorporated herein by reference in its entirety.

BACKGROUND OF THE INVENTION

A. Field of the Invention

The present invention relates generally to pharmaceutical formulations and, more particularly, to therapeutic formulations of small molecule drugs having improved solubility, stability, and bioavailability, and to methods of using such pharmaceutical formulations to treat various diseases, conditions, and disorders.

B. Description of the Related Art

While many small molecule drugs are orally bioavailable, parenteral injection is also used in situations where the drug has insufficient oral bioavailability, the patient is unable to accept drugs orally, or there is a need for more rapid onset of drug action. For example, administration of benzodiazepines for emergency treatment of epileptic seizures, catecholemines for allergic reactions, and "triptans" for the treatment of migraine headaches represent situations where oral administration is not as efficient or advisable and thus, the drugs must be administered via a non-oral route, often parenteral administration.

Standard practice for preparing formulations containing small molecule drugs has been to develop aqueous solutions for parenteral injection. The primary reason is that the majority of the human body is composed of water, including blood plasma which is an aqueous environment. Accordingly, there is a natural tendency to administer a drug formulation that is compatible with the environment that the drug is intended to reach. Several small molecule drugs, however, have limited solubility and poor stability in such aqueous environments. This problem has been solved, at least in part, by including co-solvents and/or stabilizers into the formulation to more efficiently solubilize and stabilize the small molecule drug in an aqueous solution.

An example of some of the difficulties associated with parenteral injection of small molecule drugs can be seen with diazepam. This drug, which is used for emergency treatment of epileptic seizures, has been hampered by its poor aqueous solubility. Thus, the currently available emergency treatment consists of a rectal gel. An attempt has also been made to develop a large-volume (up to 3 mL) intramuscular injection based on an aqueous formulation with co-solvents (larger volumes are needed due to lower solubility of diazepam). However, the development of this drug has been limited by the difficulty in delivering a deep, large volume intramuscular injection to a convulsing patient, as well as the pain associated with such a large dosage volume.

Further, due to the stability issues of small molecule drugs in aqueous environments, current products are oftentimes sold as lyophilized powders that require reconstitution in an aqueous carrier prior to injection. This allows for longer shelf-life of the drug. Some products are even sold as liquids that require further dilution prior to injection with sterile water, phosphate buffer solution, or isotonic saline.

Due to the limited aqueous solubility of therapeutically relevant benzodiazepine drugs (e.g., diazepam) there have been previous attempts to formulate these drugs as non-aqueous compositions. For example, U.S. Pat. No. 8,946,208 (Castile et al.) describes compositions for intranasal administration wherein a small molecule drug (e.g., diazepam) is dissolved in a non-aqueous vehicle comprising propylene glycol and one additional non-aqueous solvent selected from a group including N-methylpyrrolidone (NMP) and dimethylsulfoxide (DMSO). The pharmaceutical compositions for intranasal administration described by Castile et al. can be highly concentrated, with examples citing diazepam concentrations ranging up to 200 mg/mL and preferred embodiments directed to 50 mg/mL concentrations. The nasal spray formulations described by Castile et al. do not address the problem of poor water solubility encountered by the drug when it is administered to a patient, and specifically the problem of low bioavailability that occurs when such a formulation is administered to the patient as a highly concentrated injectable formulation.

Another example is the non-aqueous small molecule compositions for parenteral injection as described in U.S. Pat. No. 9,125,805 (Patent '805). Patent '805 disclosed compositions include concentrated diazepam formulations (e.g., 50 and 100 mg/mL solutions) solubilized in non-aqueous solvents, including DMSO and NMP, with examples describing excellent long-term stability under accelerated storage conditions (40° C./75% relative humidity). However, while these formulations may exhibit excellent long-term stability when stored in a pharmaceutically relevant container-closure system (e.g., a vial, a pre-filled syringe), they exhibit poor bioavailability when injected into a patient due to the extremely low water solubility of diazepam at physiological pH, resulting in precipitation of the drug at the injection site.

The technology described in this application builds upon the previous discoveries by Xeris Pharmaceuticals (e.g., Patent '805) that solved the problem of poor water solubility and stability of many small molecule drugs, enabling the development of injectable solutions using aprotic polar solvents. However, while these formulations possessed excellent solubility of poorly water-soluble drugs such as diazepam (≥50 mg/mL), coupled with excellent long-term storage stability in vials and pre-filled syringes, the bioavailability of the active pharmaceutical ingredient (API) following injection was minimal due to the precipitation of the drug at the injection site.

Accordingly, there remains a need for a formulation that addresses the poor aqueous solubility and stability of small molecules, including benzodiazepines, while providing for improved bioavailability of highly-concentrated formulations when parenterally administered to a patient.

SUMMARY

The problem of small molecule (e.g., diazepam) precipitation at the injection site when administered as a highly-concentrated formulation is solved by the inclusion of at least one surfactant in the non-aqueous formulation, which prevents small molecule precipitation and improves the bioavailability of the drug by enhancing absorption into the systemic circulation. The present invention provides a solution to the current problems facing the use of small molecule drugs in therapeutic applications as described above. The solution is premised on solubilizing and stabilizing a small molecule drug in a non-aqueous environment and then directly injecting the solubilized drug into a patient via parenteral administration, without the need for a reconstitution and/or dilution step prior to administration. The formulation can be in liquid form. Once the formulation is prepared, it can be stored for an extended period (even in an injection device) and directly injected into a subject (e.g., human) without the reconstitution or dilution steps seen in current products. Indeed, this solution goes against the prevailing industry standard. In this regard, the inventors' solution has resulted in a more stable environment for the drug and a more efficient and effective way to provide life-saving drugs to those in need of treatment. Importantly, the inventors' discovery is widely applicable for the delivery of numerous small molecule drugs that, like diazepam, that have poor or limited stability and solubility in an aqueous environment.

The non-aqueous vehicles described in this application are suitable for preparing pharmaceutical compositions for the intracutaneous delivery of a wide range of drug compounds. Given the current description, a person having ordinary skill in the art can determine whether a particular aprotic polar solvent system is suitable for use in combination with a particular drug. For example, this can be done by measuring the solubility of the drug compound in the vehicle. The solubility can be tested by adding an excess of the drug to the vehicle and stirring the mixture for 24 hours at room temperature. Undissolved drug is then removed by filtration or centrifugation and the solution is assayed for dissolved drug content by an appropriate analytical method, such as high-performance liquid chromatography (HPLC).

Without wishing to be bound by theory, it is believed that the use of surfactants in the aprotic polar solvent formulations improve bioavailability by preventing the precipitation of the highly-concentrated small molecules (e.g., benzodiazepine) formulations when injected into a patient. Specifically, it is believed that surfactants improve solubility by entrapping drugs such as diazepam in micelles such that upon injection into an aqueous environment the surfactant facilitates diffusion of diazepam away from the injection site allowing for rapid absorption and greater bioavailability. When injecting highly-concentrated diazepam formulation into an aqueous environment at physiological pH without the use of surfactants, the diazepam partially precipitates and is slowly resolubilized and absorbed.

Certain embodiments of the invention are directed to stable precipitation resistant formulations for parenteral injection. The formulations can include (a) a biocompatible non-aqueous solvent; (b) a small molecule drug, or a salt thereof, solubilized within the non-aqueous solvent; and (c) 1, 2, 3, 4, 5, 6, 7, 8, 9, 10, 11, 12, 13, 14, 15% to 16, 17, 18, 19, 20, 21, 22, 23, 24, 25, 26, 27, 28, 29, 30% w/w (including all values and ranges there between) of a surfactant, wherein the surfactant attenuates the precipitation of the small molecule drug when injected into a subject. In certain aspects, the surfactant is present at a molar ratio of surfactant:small molecule drug of 0.5:1 to 4:1, or 1:1 to 2:1. The surfactant can be sodium deoxycholate, polysorbate 80, polysorbate 20, dodecyl maltoside, sodium dodecyl sulfate, sodium tetradecyl sulfate, alcohol ethoxylate, alkyldimethylamine oxide, or alkyl betaine. In certain aspects, the liquid formulation comprises less than 10, 9, 8, 7, 6, 5, 4, 3, 2, or 1% by weight moisture content. The formulation of claim 1, wherein the volume of the liquid formulation to be parenterally injected is 3 mL or less. The formulation can be included within a device for dispensing the formulation. In certain aspects, the device is a syringe, a pen injection device, an auto-injector device, an external or implantable pump, or a perfusion bag. The biocompatible non-aqueous solvent can be an aprotic polar solvent, an alkyl or aryl benzoate solvent, a lipid solvent, a protic solvent, or a mixture thereof. In certain aspects, the formulation includes an aprotic polar solvent, and wherein the aprotic polar solvent is dimethylsulfoxide (DMSO), dimethylformamide (DMF), ethyl acetate, n-methyl pyrrolidone (NMP), dimethyl acetamide (DMA), propylene carbonate, or mixtures thereof. In particular aspects, the aprotic polar solvent is DMSO, NMP, or a mixture thereof. The formulation can also include an aryl or alkyl benzoate solvent, and wherein the aryl or alkyl benzoate solvent is ethyl benzoate, benzyl benzoate, or mixtures thereof. The formulation can include from 0.5, 5, 10, 20, 40, 80, 160, 320 mg/mL to 350, 400, 450, 500, 550, 600, 650, 700, 750 mg/mL (including all values and ranges there between) of the small molecule drug. In certain aspects, the volume of the liquid formulation to be parenterally injected is from 1 μL to 10 μL, 10 μL to 100 μL, or 100 μL to 1 mL. In certain aspects, the small molecule drug is a benzodiazepine. In a particular aspect, the benzodiazepine is diazepam. The formulation can include 25, 50, 75, 100, 125, 150 mg/mL to 175, 200, 225, 250, 275, 300 mg/mL (including all values and ranges there between) of a benzodiazepine. The solvent can be, but is not limited to DMSO, NMP, or a mixture thereof.

Certain embodiments are directed to methods of administering the formulation of the invention to a subject in need thereof comprising parenterally injecting the formulation to the subject. In certain aspects injecting is by parenteral injection or intracutaneous injection. In certain aspects, the formulation is not diluted prior to administration.

Still other embodiments of the invention are directed to methods for treating or preventing a condition by parenterally administering to a subject in need thereof a formulation of the claimed invention having an amount of a small molecule drug effective to treat or prevent the condition.

Certain aspects are directed to methods for treating or preventing anxiety, muscle spasms, or seizures, the method including parenterally administering to a subject in need thereof a benzodiazepine formulation. The method can include administering a formulation in an injectable volume that is within a device for dispensing the formulation. The device can be a syringe, a pen injection device, an auto-injector device, an external or implantable pump, or a perfusion bag. In certain aspects, the liquid formulation includes 25 mg/mL to 300 mg/mL benzodiazepine. In a particular aspect, the benzodiazepine is diazepam. The volume of the liquid formulation to be parenterally injected can be from 1 μL to 10 μL, 10 μL to 100 μL, or 100 μL to 1 mL. In certain aspects, the liquid formulation is not diluted prior to administration.

The term "benzodiazepines" as used herein refers to the class of chemical compounds containing a bicyclic core unit in which a benzene ring is fused with a diazepine ring. Benzodiazepines are widely used lipophilic drugs that act on the central nervous system, causing sedation, decreased anxiety, muscle relaxation, and anticonvulsant actions. Non-limiting examples of benzodiazepines include diazepam, clonazepam, lorazepam, alprazolam, midazolam, and temazepam.

The term "surfactants" as used herein refers to surface-active agents which may adsorb onto the surfaces and/or interfaces of a system and alter the surface or interfacial free energy and the surface or interfacial tension. Non-limiting functions of surfactants include use as wetting agents, emulsifying agents, dispersing agents, and suspending agents. Surfactants are monomeric, amphipathic molecules possessing a characteristic structure that has both a non-polar (hydrophobic) region termed a "tail" and a polar (hydrophilic) region that termed the "head." The hydrophobic tail of the surfactant molecule is generally comprised of an unsaturated or saturated hydrocarbon chain or a heterocyclic or aromatic ring system. The hydrophilic head of the surfactant molecule is polar and depending upon the charge group present in the polar head of the surfactant, they may be classified as either non-ionic, cationic, anionic, or zwitterionic (ampholytic). If the molecule does not carry a charge group on its head, the surfactant is non-ionic. If the charge group on the polar head is positive the molecule is a cationic surfactant, while an anionic surfactant has a negative charge group on the polar head of the molecule. Zwitterionic (or ampholytic) surfactants possess both positively and negatively charged groups, and depending on the pH of the solution can exist as either cationic or anionic surfactant. Examples of anionic surfactants include, but are not limited to, carboxylate, phosphate, sulfate and sulfonate ions. Non-limiting examples of anionic surfactants sodium dodecyl sulfate (SDS), and sodium tetradecyl sulfate (STS). Non-limiting examples of cationic surfactants include alkylpyridinium chloride and alkyltrimethyl ammonium bromide. Examples of non-ionic surfactants include, but are not limited to, alcohol ethoxylate, while non-limiting examples of zwitterionic surfactants include alkyldimethylamine oxide and alkyl betaine.

The term "dissolution" as used herein refers to a process by which a material(s) in a gas, solid, or liquid state becomes a solute(s), a dissolved component(s), of a solvent, forming a solution of the gas, liquid, or solid in the solvent. In certain aspects a therapeutic agent or an excipient, e.g., an ionization stabilizing excipient, is present in an amount up to its solubility limited or is fully solubilized. The term "dissolve" refers to a gas, liquid, or solid becoming incorporated into a solvent to form a solution.

The term "excipient" as used herein refers to a natural or synthetic substance formulated alongside the active or therapeutic ingredient (an ingredient that is not the active ingredient) of a medication, included for the purpose of stabilization, bulking, or to confer a therapeutic enhancement on the active ingredient in the final dosage form, such as facilitating drug absorption, reducing viscosity, enhancing solubility, adjusting tonicity, mitigating injection site discomfort, depressing the freezing point, or enhancing stability. Excipients can also be useful in the manufacturing process, to aid in the handling of the active substance concerned such as by facilitating powder flowability or non-stick properties, in addition to aiding in vitro stability such as prevention of denaturation or aggregation over the expected shelf life.

"Small molecule drugs" in the context of the present invention are biologically active compounds (and salts thereof) that can bring about a desired, beneficial, and/or pharmacological effect on a subject. These "small molecule drugs" are organic or inorganic compounds. Therefore, the small molecule drugs in the context of the present invention are not polymeric compounds. Typically, the small molecule drugs have a molecular weight of less than approximately 1000 Daltons. Certain small molecule drugs are "moisture sensitive" in that they are increasingly unstable in the presence of water. Also, salts that can be used with the small molecule drugs are known to those skilled in the art and include salts with inorganic acids, organic acids, inorganic bases, or organic bases.

As used herein "inhibiting" or "reducing" or any variation of these terms includes any measurable decrease or complete inhibition to achieve a desired result.

As used herein "effective" or "treating" or "preventing" or any variation of these terms means adequate to accomplish a desired, expected, or intended result.

As used herein "chemical stability," when referring to a therapeutic agent, refers to an acceptable percentage of degradation products produced by chemical pathways such as oxidation and/or hydrolysis and/or fragmentation and/or other chemical degradation pathways. In particular, a formulation is considered chemically stable if no more than about 20% breakdown products are formed after one year of storage at the intended storage temperature of the product (e.g., room temperature); or storage of the product at 25° C./60% relative humidity (RH) for one year; or storage of the product at 40° C./75% relative humidity for one month, and preferably three months. In some embodiments, a chemically stable formulation has less than 20%, less than 15%, less than 10%, less than 5%, less than 4%, less than 3%, less than 2%, or less than 1% breakdown products formed after an extended period of storage at the intended storage temperature of the product.

As used herein "physical stability," when referring to a therapeutic agent, refers to an acceptable percentage of insoluble precipitates and/or aggregates (e.g., dimers, trimers, and larger forms) being formed. In particular, a formulation is considered physically stable if no more that about 15% aggregates are formed after one year of storage at the intended storage temperature of the product (e.g., room temperature); or storage of the product at 25° C./60% relative humidity for one year; or storage of the product at 40° C./75% relative humidity for one month, and preferably three months. In some embodiments, a physically stable formulation has less than less than 15%, less than 10%, less than 5%, less than 4%, less than 3%, less than 2%, or less than 1% aggregates formed after an extended period of storage at the intended storage temperature of the product.

As used herein "stable formulation" refers to a formulation where at least about 65% of the therapeutic agents (e.g., peptides or salts thereof) remain chemically and physically stable after two months of storage at room temperature. Particularly preferred formulations are those in which at least about 80%, 85%, 90%, 91%, 92%, 93%, 94%, 95%, 96%, 97%, 98%, or 99% chemically and physically stable therapeutic agent remains under these storage conditions. Especially preferred stable formulations are those which do not exhibit degradation after sterilizing irradiation (e.g., gamma, beta, or electron beam).

As used herein, "parenteral administration" refers to administration of a therapeutic agent to a patient via a route other than the alimentary canal—any administration that is not by way of the digestive tract.

As used herein, "parenteral injection" refers to the administration of therapeutic agents (e.g., peptides or small molecules) via injection under or through one or more layers of skin or mucus membranes of an animal, such as a human. Standard parenteral injections are given into the subcutaneous, intramuscular, or intradermal region of an animal, e.g., a human. These deep locations are targeted because the tissue expands more easily relative to shallow dermal sites to accommodate injection volumes required to deliver most therapeutic agents, e.g., 0.1 to 3.0 cc (mL).

The term "intracutaneous" encompasses administration into the epidermal, dermal or subcutaneous skin layer.

As used herein, the term "aprotic polar solvent" refers to a polar solvent which does not contain acidic hydrogen and thus does not act as a hydrogen bond donor. Polar aprotic solvents include, but are not limited to dimethylsulfoxide (DMSO), dimethylformamide (DMF), ethyl acetate, n-methyl pyrrolidone (NMP), dimethylacetamide (DMA), and propylene carbonate.

As used herein, the term "aprotic polar solvent system" refers to a solution wherein the solvent is a single aprotic polar solvent (for example, neat DMSO), or a mixture of two or more aprotic polar solvents (for example, a mixture of DMSO and NMP).

As used herein, "residual moisture" may refer to the residual moisture in the drug powder following preparation by the manufacturer/supplier. Typical powders often have residual moisture contents ranging from up to 10% (w/w). When these powders are dissolved in an aprotic polar solvent system, the residual moisture in the powder is incorporated into the formulation. Additionally, the aprotic polar solvents may also contain a certain level of residual moisture. For example, a freshly opened bottle of USP-grade DMSO typically contains up to 0.1% (w/w) moisture. The residual moisture is different from "added moisture," where water is intentionally added to the formulation, for example to serve as a co-solvent, or to depress the freezing point of the aprotic polar solvent system. Moisture may also be introduced into the formulation during addition of an ionization stabilizing excipient (for example, through addition of a mineral acid from an aqueous stock solution (e.g., 1N HCl)). The "total moisture" (% w/w, unless otherwise stated) in a formulation immediately following preparation is due to the contributions from both the residual moisture and the added moisture.

The use of the word "a" or "an" when used in conjunction with the term "comprising" in the claims and/or the specification may mean "one," but it is also consistent with the meaning of "one or more," "at least one," and "one or more than one."

The words "comprising" (and any form of comprising, such as "comprise" and "comprises"), "having" (and any form of having, such as "have" and "has"), "including" (and any form of including, such as "includes" and "include") or "containing" (and any form of containing, such as "contains" and "contain") are inclusive or open-ended and do not exclude additional, unrecited elements or method steps.

The term "about" or "approximately" or "substantially unchanged" are defined as being close to as understood by one of ordinary skill in the art, and in one non-limiting embodiment the terms are defined to be within 10%, preferably within 5%, more preferably within 1%, and most preferably within 0.5%. Further, "substantially non-aqueous" refers to less than 5%, 4%, 3%, 2%, 1%, or less by weight or volume of water.

As used herein "pharmaceutically acceptable" ingredient, excipient, or component is one that is suitable for use with humans and/or animals without undue adverse side effects (such as toxicity, irritation and allergic response) commensurate with a reasonable benefit/risk ratio.

As used herein "pharmaceutically acceptable carrier" means a pharmaceutically acceptable solvent, suspending agent, or vehicle for delivering a drug compound of the present invention to a mammal such as a human.

Other objects, features and advantages of the present invention will become apparent from the following detailed description. It should be understood, however, that the detailed description and the examples, while indicating specific embodiments of the invention, are given by way of illustration only. Additionally, it is contemplated that changes and modifications within the spirit and scope of the invention will become apparent to those skilled in the art from this detailed description. Other embodiments of the invention are discussed throughout this application. Any embodiment discussed with respect to one aspect of the invention applies to other aspects of the invention as well and vice versa. Each embodiment described herein is understood to be embodiments of the invention that are applicable to all aspects of the invention. It is contemplated that any embodiment discussed herein can be implemented with respect to any method or composition of the invention, and vice versa. Furthermore, compositions and kits of the invention can be used to achieve methods of the invention.

DESCRIPTION OF THE DRAWINGS

The following drawings form part of the present specification and are included to further demonstrate certain aspects of the present invention. The invention may be better understood by reference to one or more of these drawings in combination with the detailed description of the specification embodiments presented herein.

DESCRIPTION

Figure 1:
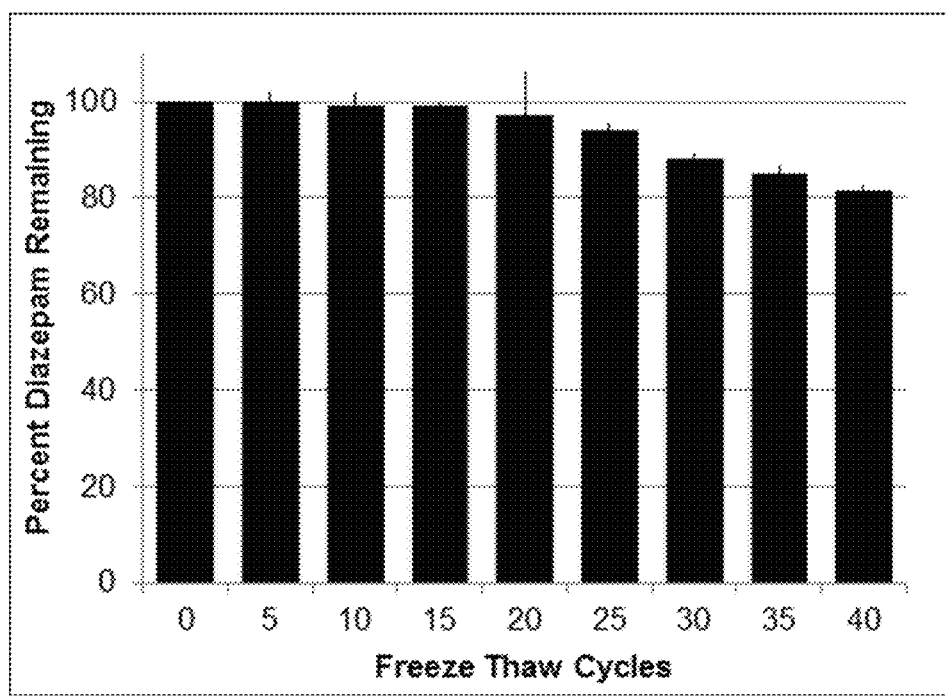
FIG. 1. Illustrates the stability of diazepam dissolved in DMSO through several freeze-thaw cycles.

The following discussion is directed to various embodiments of the invention. The term "invention" is not intended to refer to any particular embodiment or otherwise limit the scope of the disclosure. Although one or more of these embodiments may be preferred, the embodiments disclosed should not be interpreted, or otherwise used, as limiting the scope of the disclosure, including the claims. In addition, one skilled in the art will understand that the following description has broad application, and the discussion of any embodiment is meant only to be exemplary of that embodiment, and not intended to intimate that the scope of the disclosure, including the claims, is limited to that embodiment.

A. SMALL MOLECULE DRUGS

In addition to the benzodiazepines, other non-limiting small molecule drugs that can be used in the context of the present invention include epinephrine, naloxone, naltrexone, remifentanil, ganaxolone, fenfluramine, brivaracetam, apomorphine, carbidopa, levodopa, dihydroergotamine, levothyroxine, hemin, palonosetrone, sumatriptan, aprepitant, novantrone, chemotherapy small molecules (e.g., mitoxantrone), corticosteroid small molecules (e.g., methylprednisolone), immunosuppressive small molecules (e.g., azathioprine, cladribine, cyclophosphamide, methotrexate), anti-inflammatory small molecules (e.g., salicylic acid, acetylsalicylic acid, diflunisal, choline magnesium trisalicylate, salicylate, benorylate, flufenamic acid, mefenamic acid, meclofenamic acid, triflumic acid, diclofenac, fenclofenac, alclofenac, fentiazac, ibuprofen, flurbiprofen, ketoprofen, naproxen, fenoprofen, fenbufen, suprofen, indoprofen, tiaprofenic acid, benoxaprofen, pirprofen, tolmetin, zomepirac, clopinac, indomethacin, sulindac, phenylbutazone, oxyphenbutazone, azapropazone, feprazone, piroxicam, isoxicam), small molecules used to treat neurological disorders (e.g., cimetidine, ranitidine, famotidine, nizatidine, tacrine, donepizil, metrifonate, rivastigmine, selegilene, imipramine, fluoxetine, olanzapine, sertindole, risperidone, paliperidone, aripiprazole, valproate semisodium, gabapentin, carbamazepine, topiramate, phenyloin, haloperidol), and small molecules used to treat cancer (e.g., vincristine, vinblastin, paclitaxel, docetaxel, cisplatin, irinotecan, topotecan, gemcitabine, temozolomide, imatinib, bortezomib), statins (e.g., atorvastatin, amlodipine, rosuvastatin, sitagliptin, simvastatin, fluvastatin, pitavastatin, lovastatin, pravastatin, simvastatin), and other taxane derivatives. In particular embodiments, the small molecules that can be used include those that treat tuberculosis (e.g., rifampicin), small molecule anti-fungal agents (e.g., fluconazole), small molecule anti-anxiety agents and small molecule anti-convulsant agents (e.g., lorazepam), small molecule anti-cholinergic agents (e.g., atropine), small molecule β-agonist drugs (e.g., albuterol sulfate), small molecule mast cell stabilizers and small molecule agents used to treat allergies (e.g., cromolyn sodium), small molecule anesthetic agents and small molecule anti-arrhythmic agents (e.g., lidocaine), small molecule antibiotic agents (e.g., tobramycin, ciprofloxacin), small molecule anti-migraine agents (e.g., sumatriptan), and small molecule anti-histamine drugs (e.g., diphenhydramine). Further, the amount of the small molecule drugs in the dosage formulations can be varied depending on current acceptable amounts, subject/patient needs, and the like.

With respect to the biocompatible non-aqueous solvent, examples include aprotic polar solvents, alkyl or aryl benzoate solvents, lipid solvents, protic solvents, or a mixture thereof. Non-limiting examples of aprotic polar solvents include dimethylsulfoxide (DMSO), dimethylformamide (DMF), ethyl acetate, n-methylpyrrolidone (NMP), dimethyl acetamide (DMA), propylene carbonate, or mixtures thereof. In some instances, however, the formulations of the present invention do not have to include the aforementioned solvents (i.e., others can be used). In one instance, for example, the formulations do not include non-aqueous aprotic polar solvents and/or do not include non-aqueous protic solvents (e.g., polyethylene glycol (PEG), propylene glycol (PG), polyvinylpyrrolidone (PVP), methoxypropylene glycol (MPEG), glycerol, glycofurol, and mixtures thereof). As noted above, the increased solubility of the small molecule drugs can result in small dosage volumes (and, in turn, small storage devices and containers), which provides for an easier and less painful administration parenterally. Non-limiting examples of aryl or alkyl benzoate solvents include methyl benzoate, ethyl benzoate, propyl benzoate, C12-C15 alkyl benzoates, in which R is a C12-15 alkyl group, C16-17 alkyl benzoate, in which R is a C16-17 fatty alcohol group, and benzyl benzoate. A non-limiting example of a lipid is triacetin, which is the triester of glycerol and acetic acid. Non-limiting examples of protic solvents include polyethylene glycol (PEG), propylene glycol (PG), polyvinylpyrrolidone (PVP), methoxypropylene glycol (MPEG), glycerol, glycofurol, or mixtures thereof. In certain aspects, the formulation does not include a co-solvent, while in other aspects it can include a co-solvent. In one instance, the formulation can include a single/only one biocompatible non-aqueous solvent (i.e., in neat or pure form). In other aspects, the formulation includes a mixture of two, three, four, or more biocompatible non-aqueous solvents. In still additional aspects, the formulation can exclude co-solvents, salts, and other ingredients that can help with or increase the solubility of the small molecule drug in the non-aqueous solvent. For instance, the formulation can consist of or consist essentially of a small molecule drug and a non-aqueous solvent (or mixture of non-aqueous solvents) and still be directly injected through parenteral administration to a subject—with consist essentially of meaning in the context of this sentence exclusion of other ingredients that could increase the solubility of the drug within the non-aqueous solvent or mixture of non-aqueous solvents—e.g., a preservative can be included to further preserve the injectable formulation.

Further, the formulation of the present invention can be non-aqueous or substantially non-aqueous (e.g., less than 10%, 9%, 8%, 7%, 6%, 5%, 4%, 3%, 2%, 1%, 0.5% or less of total moisture (i.e. moisture present in the formulation when it is initially prepared) by weight. In some instances, the small molecule drug has previously been dried in the presence of a buffer prior to being solubilized in the non-aqueous solvent. As explained below, this can add to the stability of the small molecule drug. In some instances, the dried small molecule drug has a pH memory that is about equal to the pH of the small molecule drug in the presence of the aqueous buffer such that the pH of the small molecule drug that is solubilized in the biocompatible non-aqueous solvent is about equal to the pH of the small molecule drug in the presence of the buffer. The memory pH can be 1, 2, 3, 4, 5, 6, 7, 8, 9, 10, 11, or more or can be a range of 1 to 3, 2 to 4, 3 to 5, 4 to 6, 5 to 7, 6 to 8, 7 to 9, 8 to 10 or 9 to 11. In certain aspects, the buffer is a non-volatile buffer (non-limiting examples of which include glycine buffers, citrate buffers, or phosphate buffers, or a mixture thereof). In other instances, the buffer can be a volatile buffer. Further, the moisture content of the small molecule drug can be less than 5%, 4%, 3%, 2%, 1%, 0.5% or less w/w.

In certain aspects, the formulation includes from 0.5 mg/mL to about 300 mg/mL, 10 mg/mL to 50 mg/mL, 20 mg/mL to 50 mg/mL, 5 mg/mL to 15 mg/mL, or 0.5 mg/mL to 2 mg/mL of the small molecule drug. In some instances, the amount of the small molecule drug can be as high as 400, 500, 600, 700, 800, 900, 1000, 2000, or 3000 mg/mL or more. One of the unique aspects of the present formulation is that the formulation can have a high content of the drug, yet the dosage of the formulation can be relatively low (e.g., 0.1 μL, 1 μL, 10 μL, 20 μL, 50 μL, 75 μL, 100 μL, 200 μL, 300 μL, 400 μL, 500 μL, 600 μL, 700 μL, 800 μL, 900 μL, 1 mL, 2 mL, or 3 mL, or more as needed (e.g., 4, 5, 6, 7, 8, 9, 10 mL or more). In certain instances, the volume of the liquid formulation to be parenterally injected is 3 mL or less (e.g., 3, 2.5, 2, 1.5, 1, 0.5, 0.1 mL or less) or is from 0.1 μL to 3 mL or from 0.1 μL to 1 μL or from 1 μL to 10 μL or from 10 μL to 1 mL or from 0.1 μL to 2.5 mL or from 0.1 μL to 2 mL or from 0.1 μL to 1.5 mL or from 0.1 μL to 1 mL or from 0.1 μL to 0.5 mL or from 0.1 μL to 0.1 mL. Another unique aspect of the present formulation is that it can be contained in a container or device, be stored, and be immediately ready for parenteral injection on an as-needed basis without having to reconstitute or dilute the formulation. The device can be a syringe, a pen injection device, an auto-injector device, a device that can pump or administer the formulation (e.g., automatic or non-automatic external pumps, implantable pumps, etc.) or a perfusion bag. Also contemplated for use in the formulations are additional ingredients/pharmaceutical excipients, non-limiting example of which include: antioxidants (examples include ascorbic acid, cysteine, methionine, monothioglycerol, sodium thiosulfate, sulfites, BHT, BHA, ascorbyl palmitate, propyl gallate, or vitamin E); chelating agents (examples include EDTA, EGTA, tartaric acid, glycerin, or citric acid); or preservatives (examples include alkyl alcohols, benzyl alcohol, a methyl paraben, or a propyl paraben or mixtures thereof). The formulation can be in liquid form, semi-solid form, or gel form. As discussed below, the formulation can have a desired viscosity range (in one non-limiting example, such a range could be between 0.5 to 15 cps). The formulation can be such that at least 65% of the small molecule drug within the formulation remains chemically and physically stable when the formulation is stored at room temperature for two months or at least 80% of the therapeutic agent within the formulation remains chemically and physically stable when the formulation is stored at room temperature for two months.

In one particular aspect of the present invention, there is disclosed a stable liquid formulation for parenteral injection comprising diazepam, or a salt thereof, at least one surfactant, and a biocompatible non-aqueous solvent, wherein the diazepam and the surfactant(s) are solubilized within the non-aqueous solvent, wherein the total water content of the formulation when prepared is less than 5% w/w, wherein the volume of the formulation to be parenterally injected is between 50 µL to 1000 µL or any range therein (e.g., 75 µL, 100 µL, 150 µL, 200 µL, 300 µL, 400 µL, 500 µL, 600 µL, 700 µL, 800 µL, 900 µL, etc.). In a further aspect the formulation can include additional excipients. As explained above, such a formulation can be comprised in a container selected from a sealed syringe, a sealed pen injection device, a sealed auto-injector device, or a pump. Also, as explained above, the diazepam can be dried in the presence of a buffer prior to being solubilized in the non-aqueous solvent. This can provide the dried diazepam with a pH memory that is about equal to the pH of diazepam in the presence of the aqueous buffer such that the pH of the diazepam that is solubilized in the biocompatible non-aqueous solvent is about equal to the pH of the diazepam in the presence of the aqueous buffer (e.g., the aforementioned non-volatile buffers such as glycine buffers, citrate buffers, or phosphate buffers, or a mixture thereof).

Still further, the formulations of the present invention can include one or more other excipients in addition to the surfactant(s). In some embodiments, the other excipient is selected from sugars, starches, sugar alcohols, antioxidants, chelators, polymers, and preservatives. Examples of suitable sugars excipients include, but are not limited to trehalose, glucose, sucrose, etc. Examples of suitable starches for stabilizing excipients include, but are not limited to, hydroxyethyl starch (HES). Examples of suitable sugar alcohols (also referred to as polyols) include, but are not limited to, mannitol and sorbitol. Examples of suitable antioxidants include, but are not limited to, ascorbic acid, cysteine, methionine, monothioglycerol, sodium thiosulphate, sulfites, BHT, BHA, ascorbyl palmitate, propyl gallate, N-acetyl-L-cysteine (NAC), and Vitamin E. Examples of suitable chelators include, but are not limited to, EDTA, EDTA disodium salt (edetate disodium), tartaric acid and salts thereof, glycerin, and citric acid and salts thereof. Examples of suitable inorganic salts include sodium chloride, potassium chloride, calcium chloride, magnesium chloride, calcium sulfate, and magnesium sulfate. Examples of suitable preservatives include, but are not limited to, benzyl alcohols, methyl parabens, propyl parabens, and mixtures thereof. Additional formulation components include local anesthetics, such as lidocaine or procaine. In some embodiments, the additional stabilizing excipient is present in the formulation in an amount ranging from about 0.05% (w/v) to about 60% (w/v), from about 1% (w/v) to about 50% (w/v), from about 1% (w/v) to about 40% (w/v), from about 1% (w/v) to about 30% (w/v), from about 1% (w/v) to about 20% (w/v), from about 5% (w/v) to about 60% (w/v), from about 5% (w/v) to about 50% (w/v), from about 5% (w/v) to about 40% (w/v), from about 5% (w/v) to about 30% (w/v), from about 5% (w/v) to about 20% (w/v), from about 10% (w/v) to about 60% (w/v), from about 10% (w/v) to about 50% (w/v), from about 10% (w/v) to about 40% (w/v), from about 10% (w/v) to about 30% (w/v), or from about 10% (w/v) to about 20% (w/v). In some embodiments, the additional stabilizing excipient is present in the formulation in an amount that is about, at most, or at least 0.1, 0.5, 1, 2, 3, 4, 5, 6, 7, 8, 9, 10, 15, 20, 25, 30, 35, 40, 45, 50, 55, or 60% (w/v).

B. METHOD OF MAKING

In certain embodiments, the invention also provides methods of formulating compositions comprising a small molecule drug with one or more of: a pharmaceutically acceptable solvent; a surfactant; a carrier; a solubilizer; an emulsifier; a preservative; and/or other excipient. Such compositions may contain an effective amount of at least one small molecule drug. Thus, the use of one or more small molecule drugs in the preparation of a pharmaceutical composition of a medicament is also included. Acceptable formulation components for pharmaceutical preparations are nontoxic to recipients at the dosages and concentrations employed. Formulation components are present in concentrations that are acceptable to the site of administration. The pharmaceutical composition to be used for in vivo administration is typically sterile. Sterilization may be accomplished by filtration through sterile filtration membranes.

Once the pharmaceutical composition of the invention has been formulated, it may be stored in sterile vials as a solution. Such formulations may be stored in a ready-to-use form. The components used to formulate the pharmaceutical compositions are preferably of high purity and are substantially free of potentially harmful contaminants (e.g., at least National Food (NF) grade, generally at least analytical grade, and more typically at least pharmaceutical grade). Moreover, compositions intended for in vivo use are usually sterile.

Therapeutically effective doses will be easily determined by one of skill in the art and will depend on the severity and course of the disease, the patient's health and response to treatment, the patient's age, weight, height, sex, previous medical history and the judgment of the treating physician.

Other embodiments of the present invention are directed to methods of stably formulating a small molecule drugs (e.g., a benzodiazepine drug) comprising the steps of: dissolving the drug (e.g., benzodiazepine) and surfactant (and any other additional excipients) in DMSO—the order of dissolution may or may not be of importance.

C. METHOD OF TREATING

In a further aspect of the present invention there is disclosed a method for treating or preventing a condition, disease, disorder, etc. comprising administering to a subject in need thereof a formulation(s) of the present invention in an amount effective to treat or prevent the condition, disease, disorder, etc. Any suitable dosage of a therapeutic agent (e.g., small molecule) may be administered in the methods of the present invention. Depending on the small molecule(s) comprising the therapeutic formulation, use will be governed by the indications for which they are approved.

As a non-limiting example, benzodiazepines such as diazepam are indicated for short-term relief for the symptoms of anxiety disorders or for the management of anxiety disorders. Indications also include the relief of symptoms of acute alcohol withdrawal, including tremor, impeding or acute delirium tremens, hallucinosis, and acute agitation, as well as use as an adjunct for the relief of skeletal muscle spasm. Further indications include status epilepticus, and severe recurrent or convulsive seizures. Injectable diazepam may also be used in the management of selected patients with epilepsy, on stable regimens of AEDs, who may require intermittent use of diazepam to control bouts of increased seizure activity.

The dosage administered will, of course, vary depending upon known factors, such as the pharmacodynamic characteristics of the particular compound, salt, or combination; the age, health, or weight of the subject; the nature and extent of symptoms; the metabolic characteristics of the drug and patient, the kind of concurrent treatment; the frequency of treatment; or the effect desired. In certain aspects epileptic seizures can be treated by administering a formulation described herein comprising an effective amount of diazepam.

Though well-known for their use in the treatment of seizures, benzodiazepines such as diazepam can also be used for the prevention of seizures. One reported example describing the use of a benzodiazepine as a prophylactic/preventative measure for eliminating the occurrence of seizures is the use of diazepam for the prevention of febrile seizures. Shinnar et al., in *Pediatric Epilepsy: Diagnosis and Therapy, Chapter 19, Febrile Seizures,* 2007, 3:293-301 (hereinafter "Shinnar") teaches that diazepam can be administered at the onset of fever, but prior to the onset of seizures to prevent febrile seizures. Shinnar states: "Despite febrile status epilepticus representing only 5% of febrile seizures, it accounts for approximately one quarter of all episodes of childhood status epilepticus, and more than two thirds of status epilepticus cases in the second year of life," (Shinnar, page 293). "Two distinct approaches to the treatment of febrile seizures have developed based on the perceived immediate and long-term risks of febrile seizures. One approach is based on the old idea that febrile seizures are harmful and may lead to the development of epilepsy; this approach is aimed at preventing febrile seizures by using either intermittent or chronic treatment with medications. The second approach is based on the epidemiological data that febrile seizures are benign; the only concern focusing on aborting febrile seizures to prevent status epilepticus." (Shinnar, page 297, emphasis added). "Diazepam, given generally orally or rectally at the time of onset of a febrile illness has demonstrated a statistically significant, yet clinically modest, ability to reduce the probability of a febrile seizure." (Shinnar, page 298, emphasis added).

Knudsen in *Archives of Disease in Childhood,* 1985 Vol. 60, pp. 1045-1049. (hereinafter "Knudsen") teaches that non-orally administered diazepam provides effective prophylactic seizure control and reduces incidence of recurrence in high and intermediate risk children. Knudsen states: "Our recent study indicated that short term diazepam prophylaxis reduced the 18 month recurrence rate for 39% to 12% and thus prevented two thirds of all further febrile fits. Stratification showed a remarkably wide range of recurrence rates in untreated children, a uniformLy low recurrence rate in response to diazepam prophylaxis at times of fever, and an appreciable difference in the efficacy of prophylaxis, in terms of risk reduction." (Knudson, page 1048, emphasis added).

As described in the prior art, the use of non-orally administered diazepam, for example, the commercially available diazepam sold under the trade name Diastat® is administered for prevention of seizures.

D. METHOD OF ADMINISTERING

Also disclosed is a method of administering the formulations of the present invention by parenteral administration of the formulation to a subject in need thereof. The administration can be performed without having to reconstitute and/or dilute the formulation. Further, the administration can be performed with a syringe, a pen injection device, an auto-injector device, a pump, or a perfusion bag. Also, the formulation can be stored in said syringe, pen injection device, auto-injector device, pump, or perfusion bag, which can then be immediately used (again without having to reconstitute and/or dilute the formulation). Further, and as noted above, the amount of the formulation being administered can range from 1 µL, 10 µL, 20 µL, 50 µL, 75 µL, 100 µL, 200 µL, 300 µL, 400 µL, 500 µL, 600 µL, 700 µL, 800 µL, 900 µL, 1 mL, 2 mL, 3 mL, 4 mL, 5 mL, 6 mL, 7 mL, 8 mL, 9 mL, or 10 mL, or more as needed. In certain aspects, the formulations are such that the small molecule drug remains stable and solubilized (i.e., no coalescence or crystallization of the small molecule drug) and when stored at room temperature (approximately 20-25° C.) for at least 1, 2, 3, 4, 5, 6, 7, 8, 9, 10, 11, or 12 months.

E. EXAMPLES

The following examples as well as the figures are included to demonstrate certain embodiments of the invention. It should be appreciated by those of skill in the art that the techniques disclosed in the examples or figures represent techniques discovered by the inventors to function well in the practice of the invention, and thus can be considered to constitute a mode for its practice. However, those of skill in the art should, in light of the present disclosure, appreciate that many changes can be made in the specific embodiments which are disclosed and still obtain a like or similar result without departing from the spirit and scope of the invention.

Some embodiments of the present disclosure will be described in greater detail by way of specific examples. The following examples are offered for illustrative purposes, and are not intended to limit any present invention in any manner. For example, those of skill in the art will readily recognize a variety of noncritical parameters that can be changed or modified to yield essentially the same results.

Example 1

In this example, either 1% (w/v) or 2% (w/v) sodium deoxycholate (SDC)(CAS 302-95-4) was dissolved in dimethyl sulfoxide (DMSO)(CAS 67-68-5) alone, or DMSO containing 5% (v/v) benzyl alcohol (BA)(CAS 100-51-6), followed by the dissolution of diazepam to a concentration of 100 mg/mL (CAS 439-14-5). Diazepam formulations were screened for their ability to prevent diazepam precipitation using an anti-precipitation assay coupled with reversed-phase high performance liquid chromatography (RP-HPLC).

The anti-precipitation assay used to screen diazepam formulations consisted of diluting diazepam into a simulated extracellular fluid (SEF), such that there was a 50× dilution of the formulation solvent. The SEF consisted of 0.7 mM magnesium chloride (CAS 7786-30-3), 1.2 mM calcium chloride (CAS 10043-52-4), 2.0 mM potassium chloride (CAS 7447-40-7), 2.0 mM monopotassium phosphate (CAS 7778-77-0), 0.5 mM sodium sulfate (CAS 7757-82-6), 104 mM sodium chloride (CAS 7440-23-5), and 28.3 mM sodium bicarbonate (CAS 144-55-8). After diluting the diazepam formulation into SEF, the sample was mixed by inverting several times, and the sample was allowed to equilibrate for 10 minutes. The precipitate was collected by centrifugation and the soluble diazepam content was measured in the supernatant by RP-HPLC. Greater solubility in the supernatant is expected to translate into better dissolution of diazepam away from the injection site following subcutaneous administration.

The RP-HPLC method used to determine soluble diazepam was an isocratic method with a mobile phase consisting of 20% (v/v) 3.2 mM ammonium formate (CAS 540-69-2) and 80% (v/v) methanol (CAS 67-56-1). A C18 column (Luna™, Phenomenex, 3.9 mm I.D.×150 mm length, 5 micron particle size) was used with a column temperature of 40° C., a 0.6 mL/min flow rate, a 5-µL sample injection volume, and 230-nm detection wavelength.

Sample formulations containing SDC significantly improved diazepam recovery in the anti-precipitation assay (Table 1). Samples without SDC had 11.4% and 9.1% diazepam recovery, respectively, with and without the addition of BA to the formulation. Adding 1% (w/v) SDC to the formulation improved diazepam recovery by a factor of 2.6 and 2% (w/v) SDC improved recovery by a factor of 4.1. An improvement in the recovery of soluble diazepam measured using the anti-precipitation assay and RP-HPLC is expected to translate into improved dissolution of diazepam from the injection site and the prevention of diazepam precipitation following subcutaneous administration. Accordingly, improved dissolution is expected to yield a more desirable pharmacokinetic profile with rapid absorption and slowed elimination.

TABLE 1

Diazepam formulations prepared with sodium deoxycholate in DMSO prevented diazepam precipitation in SEF.

| Form. | Diazepam mg/mL | % SDC (w/v) | % DMSO (v/v) | % BA (v/v) | % Diazepam Recovered |
|---|---|---|---|---|---|
| 1 | 100 | 0% | 100% | 0% | 9.1 ± 2.2 |
| 2 | 100 | 0% | 95% | 5% | 11.4 ± 1.8 |
| 3 | 100 | 1% | 95% | 5% | 29.3 ± 0.4 |
| 4 | 100 | 2% | 95% | 5% | 46.8 ± 3.6 |

Example 2

In this example, either 1%, 10%, 20%, or 30% (v/v) Polysorbate 80 (PS80)(CAS 9005-65-5) was dispersed into DMSO with 5% (v/v) BA, followed by dissolving diazepam at a concentration of 50, 75 or 100 mg/mL. Diazepam formulations containing PS80 were screened for their ability to prevent diazepam precipitation using an anti-precipitation assay, followed by RP-HPLC (as detailed above in Example 1).

Sample formulations containing PS80 significantly improve diazepam recovery in the anti-precipitation assay (Table 2). When diazepam was dissolved at 100 mg/mL into DMSO with 5% BA and increasing concentrations of PS80 (up to 30% (v/v)), the highest concentration of PS80 yielded the best diazepam recovery. 30% (v/v) PS80 improved diazepam recovery by a factor of 7.9. When diazepam was dissolved at 75 mg/mL into DMSO with 5% (v/v) BA and increasing concentrations of PS80 (up to 30% (v/v)), the highest concentration of PS80 yielded the best diazepam recovery. Thirty (30) percent PS80 improved diazepam recovery by a factor of 8.4. Similarly, when diazepam was dissolved at 50 mg/mL into DMSO and 5% (v/v) BA with 20% (v/v) PS80, diazepam recovery was improved by a factor of 8.8.

Data in Table 2 indicates that with a fixed concentration of diazepam (either 50, 75 or 100 mg/mL), the percent of recoverable diazepam increases with the PS80 concentration. The data indicate that there is an optimal ratio between PS80 and diazepam that maximizes diazepam solubility in SEF. In the case of PS80, a ~1:1 molar ratio of diazepam and PS80 prevents precipitation in SEF.

TABLE 2

Diazepam formulations prepared with PS80 in DMSO prevented diazepam precipitation in SEF.

| Form. | Diazepam mg/mL | % PS80 (v/v) | % DMSO (v/v) | % BA (v/v) | % Diazepam Recovered |
|---|---|---|---|---|---|
| 1 | 100 | 0% | 100% | 0% | 9.1 ± 2.2 |
| 2 | 100 | 0% | 95% | 5% | 11.4 ± 1.8 |
| 3 | 100 | 1% | 94% | 5% | 5.8 ± 11.0 |
| 4 | 100 | 10% | 85% | 5% | 37.6 ± 7.4 |
| 5 | 100 | 20% | 75% | 5% | 47.9 ± 2.5 |
| 6 | 100 | 30% | 65% | 5% | 90.3 ± 1.6 |
| 7 | 75 | 10% | 85% | 5% | 60.4 ± 3.2 |
| 8 | 75 | 20% | 75% | 5% | 72.5 ± 4.4 |
| 9 | 75 | 30% | 65% | 5% | 96.3 ± 7.6 |
| 10 | 50 | 10% | 85% | 5% | 72.9 ± 2.7 |
| 11 | 50 | 20% | 75% | 5% | 100.7 ± 4.7 |

Example 3

In this example, either 1%, 5%, 10%, or 17.7% (w/v) of dodecyl maltoside (DM)(CAS 69227-93-6) was dissolved DMSO with 5% (v/v) BA, followed by dissolving diazepam at a concentration of 50, 75 or 100 mg/mL. Diazepam formulations containing DM were screened for their ability to prevent diazepam precipitation using an anti-precipitation assay and RP-HPLC (as detailed above in Example 1).

Shown in Table 3 are the percent-diazepam recovery data for formulations prepared with DM. For each concentration of diazepam (50, 75 or 100 mg/mL), increasing concentrations of DM increased the percent of diazepam that remained soluble when the formulation was diluted into SEF. For example, diazepam at 50 mg/mL dissolved into DMSO with 5% BA and 17.7% (w/v) DM had nearly 100% diazepam solubility in SEF. Like PS80, the data in Table 3 suggest that there is an ideal ratio that prevents diazepam precipitation, and in this example the ratio of DM to diazepam is ~2:1.

TABLE 3

Diazepam formulations prepared with DM in DMSO prevented diazepam precipitation in SEF.

| Form. | Diazepam mg/mL | % DM (w/v) | % DMSO (v/v) | % BA (v/v) | % Diazepam Recovered |
|---|---|---|---|---|---|
| 1 | 100 | 0% | 100% | 0% | 9.1 ± 2.2 |
| 2 | 100 | 0% | 95% | 5% | 11.4 ± 1.8 |

TABLE 3-continued

Diazepam formulations prepared with DM in DMSO prevented diazepam precipitation in SEF.

| Form. | Diazepam mg/mL | % DM (w/v) | % DMSO (v/v) | % BA (v/v) | % Diazepam Recovered |
|---|---|---|---|---|---|
| 3 | 100 | 1% | 95% | 5% | 22.5 ± 1.1 |
| 4 | 100 | 5% | 95% | 5% | 32.8 ± 2.1 |
| 5 | 100 | 10% | 95% | 5% | 46.4 ± 2.9 |
| 6 | 75 | 5% | 95% | 5% | 36.2 ± 0.5 |
| 7 | 75 | 10% | 95% | 5% | 51.1 ± 0.6 |
| 8 | 75 | 17.7% | 95% | 5% | 75.1 ± 2.8 |
| 9 | 50 | 5% | 95% | 5% | 44.3 ± 1.4 |
| 10 | 50 | 10% | 95% | 5% | 68.5 ± 0.4 |
| 11 | 50 | 17.7% | 95% | 5% | 97.9 ± 1.2 |

Example 4

In this example, either 0% or 2% (v/v) of polysorbate 20 (PS20)(CAS 9005-64-5) was dispersed into DMSO with 5% (v/v) BA, or DMSO with 5% (v/v) BA and 5% (v/v) NMP, followed by dissolving diazepam at a drug concentration of 100 mg/mL. Diazepam formulations containing PS20 were screened for their ability to prevent diazepam precipitation using an anti-precipitation assay and RP-HPLC (as detailed above in example 1).

Diazepam formulations containing PS20 significantly improved diazepam recovery in the anti-precipitation assay (Table 4). Inclusion of 1% (v/v) PS20 was not sufficient to prevent diazepam precipitation compared to formulations without the excipient. However, inclusion of 2% (v/v) PS20 improved diazepam recovery by a factor of 2.9. Diazepam formulations containing PS20 and 5% (v/v) NMP were significantly more effective at preventing diazepam precipitation than those without NMP. 1% (v/v) PS20 and 5% (v/v) NMP in the formulation improved diazepam recovery by a factor of 4.1, and inclusion of 2% (v/v) PS20 with 5% (v/v) NMP improved recovery by a factor of 5.4.

TABLE 4

Diazepam formulations prepared with PS20 in DMSO prevented diazepam precipitation in SEF.

| Form. | Diazepam mg/mL | % PS20 (w/v) | % DMSO (v/v) | % BA (v/v) | % NMP (v/v) | % Diazepam Recovered |
|---|---|---|---|---|---|---|
| 1 | 100 | 0% | 100% | 0% | 0% | 9.1 ± 2.2 |
| 2 | 100 | 0% | 95% | 5% | 0% | 11.4 ± 1.8 |
| 3 | 100 | 1% | 94% | 5% | 0% | 9.9 ± 3.4 |
| 4 | 100 | 2% | 93% | 5% | 0% | 32.9 ± 6.9 |
| 5 | 100 | 1% | 89% | 5% | 5% | 46.3 ± 2.8 |
| 6 | 100 | 2% | 88% | 5% | 5% | 61.3 ± 3.9 |

Example 5

In this example, 10% (w/v) or less of sodium dodecyl sulfate (SDS) (CAS 151-21-3) was dissolved in DMSO with 5% (v/v) BA, followed by dissolving diazepam at a concentration of 50, 75 or 100 mg/mL. Diazepam formulations containing SDS were screened for their ability to prevent diazepam precipitation using an anti-precipitation assay and RP-HPLC (as detailed above in example 1).

Shown in Table 5 are the percent-diazepam recovery data after the formulations prepared with SDS were diluted into SEF. For each concentration of diazepam (50, 75, or 100 mg/mL), increasing concentrations of SDS increased the percent of diazepam that remained soluble when diluted into SEF. When 100 mg/mL of diazepam was dissolved into DMSO with 5% (v/v) BA and 10% (w/v) SDS is diluted in SEF, the amount of recovered diazepam improved by a factor of 8.2 over diazepam in DMSO and 5% (v/v) BA without SDS. As the concentration of diazepam was decreased, the amount of SDS required to maintain diazepam solubility when diluted into SEF also decreased. The data in Table 5 suggest that there is an ideal ratio that prevents diazepam precipitation, and in this example the molar ratio of SDS to diazepam was ~1:1.

TABLE 5

Diazepam formulations prepared with SDS in DMSO prevented diazepam precipitation in SEF.

| Form. | Diazepam mg/mL | % SDS (w/v) | % DMSO (v/v) | % BA (v/v) | % Diazepam Recovered |
|---|---|---|---|---|---|
| 1 | 100 | 0% | 100% | 0% | 12.8 ± 0.2 |
| 2 | 100 | 0% | 95% | 5% | 11.4 ± 1.8 |
| 3 | 100 | 10% | 95% | 5% | 93.6 ± 4.5 |
| 4 | 100 | 8% | 95% | 5% | 81.9 ± 1.7 |
| 5 | 100 | 6% | 95% | 5% | 66.7 ± 2.1 |
| 6 | 100 | 4% | 95% | 5% | 51.9 ± 0.6 |
| 7 | 75 | 8% | 95% | 5% | 93.4 ± 1.6 |
| 8 | 75 | 6% | 95% | 5% | 68.0 ± 1.2 |
| 9 | 75 | 4% | 95% | 5% | 52.2 ± 3.2 |
| 10 | 50 | 8% | 95% | 5% | 95.5 ± 1.5 |
| 11 | 50 | 6% | 95% | 5% | 99.2 ± 3.4 |
| 12 | 50 | 4% | 95% | 5% | 92.3 ± 2.4 |
| 13 | 50 | 2% | 95% | 5% | 54.8 ± 0.9 |

Example 6

Diazepam formulations (100 mg/mL) prepared in DMSO and 5% (v/v) BA (and including different surfactants) were sealed in 2 mL CZ vials (Crystal-Zenith, West Pharmaceuticals, PA, USA) with 13 mm FluroTec® stoppers (rubber stoppers coated with a fluorocarbon film, produced by West Pharmaceuticals), and stored at 40° C./75% relative humidity for 90 days. A diazepam formulation was also prepared with 2% (v/v) PS20, 5% (v/v) BA, and 5% (v/v) NMP in DMSO. Sealed CZ vials were packaged in foil pouches for the stability study. All formulations were compared with 100 mg/mL diazepam dissolved in DMSO (containing 5% (v/v) BA). The stability of the formulations are presented as percent diazepam remaining (±standard deviation) in Table 6 below.

TABLE 6

The stability of diazepam dissolved in DMSO with various excipients at 40° C./75% relative humidity. Stability data is given as the average (±standard deviation) % purity of the diazepam peak for N = 3 replicates.

| Solvent System | Excipients | Day 0 | Day 90 |
|---|---|---|---|
| DMSO + 5% (v/v) BA | None | 100 | 95.3 ± 0.4 |
| DMSO + 5% (v/v) BA | 10% (v/v) PS80 | 100 | 98.8 ± 0.2 |
| DMSO + 5% (v/v) BA | 10% (w/v) SDS | 100 | 97.1 ± 0.1 |
| DMSO + 5% (v/v) BA | 2% (w/v) SDC | 100 | 91.0 ± 0.1 |
| DMSO + 5% (v/v) BA | 2% (v/v) PS20 | 100 | 100 ± 0.2 |
| DMSO + 5% (v/v) BA | 2% (v/v) PS20 + 5% (v/v) NMP | 100 | 95.6 ± 0.2 |

Diazepam dissolved in the DMSO-BA solvent system (with no additional excipients) experienced a 4.2% loss of diazepam purity in the first 30 days when stored at 40° C. and 75% relative humidity, but remained at ~95% for the duration of the study. Diazepam formulations prepared with excipients of 10% (v/v) PS80, 10% (w/v) SDS, and 2% (v/v) PS20 exhibited no less than 97.1% diazepam peak purity remaining at the end of the 90-day study. These formulations demonstrated enhanced stability compared to diazepam in DMSO and 5% (v/v) benzyl alcohol (with no additional excipients). Diazepam formulations prepared with 2% (v/v) PS20 and 5% (v/v) NMP exhibited stability comparable to that observed the DMSO-BA solvent system without added excipients. Finally, diazepam formulations prepared with 2% (w/v) SDC had 91% diazepam peak purity remaining at the conclusion of the 90-day stability study.

Example 7

The stability of the diazepam formulation in a DMSO-BA solvent system was studied through 40 freeze-thaw cycles. Diazepam (100 mg/mL) was dissolved into DMSO containing 5% (v/v) BA and sealed in 2 mL CZ vials with 13 mm FluroTec™ stoppers as described above. Three vials of diazepam formulation were sealed in an aluminum foil pouch and stored in a −20° C. freezer for 2 hours. Following storage the pouch was placed at room temperature and allowed to thaw for 2 hours. This process was repeated at a rate of three freeze-thaw cycles per day, where the third freeze cycle was left overnight. Following several days of freeze-thaw cycles, 2 µL of diazepam formulation was removed for analysis by RP-HPLC. Data shown in FIG. 1 shows the percent of diazepam remaining ±standard deviation in 5 freeze-thaw cycle intervals.

No significant loss of diazepam was measured following 20 freeze-thaw cycles. However, after 25 cycles the percent of diazepam remaining was significantly different from the pre-frozen sample (bar 0, $p<0.05$). With each successive interval of 5 freeze-thaw cycles, the percent of diazepam remaining decreased. After 40 cycles, there was 81.7±0.5% of diazepam remaining.

Example 8

In this example the pharmacokinetic (PK) profile of several diazepam-DMSO formulations (with and without excipients) were evaluated in a rat model. Studies were conducted in adult male Sprauge-Dawley rats (HillTop Lab Animals, Inc., Scottsdale, Pa.) between 8 and 10 weeks of age and between 275 to 325 grams, with at least 5 rats per group. Rats were housed individually in stainless steel cages and identified numerically via a permanent marker applied to the tail. Rats were observed twice-daily during acclimation and any abnormal health findings recorded. Animals were fed standard rodent chow and water during the acclimation period, but fasted overnight prior to study initiation. The animals were allowed to acclimatize for 1 week prior to the study.

Test articles for the pharmacokinetics study are described in Table 7. The study contained two commercially available diazepam formulations as comparators—Diastat® rectal diazepam (Valeant Pharmaceuticals) and Hospira's intramuscular (IM) diazepam formulation. Rats were weighed prior to study initiation to accurately administer the study dose of 3.5 mg/kg. Group 1 was dosed rectally with Diastat and group 2 received an IM injection of diazepam in the rear thigh muscle. Groups 3 through 6 were dosed subcutaneously (SC) in the mid-scapular region with diazepam using 1 of the 4 test formulations. Whole blood samples were collected in vials with $K_2$ EDTA from each rat via the jugular vein at time 0 (pre-dose), 10, 20, 30, 45, 60, and 120 minutes. Whole blood samples were centrifuged (3000 rpm, 15 minutes) and plasma was harvested. Plasma samples were frozen at −70° C. for future diazepam and nordiazepam analysis.

TABLE 7

Test articles and dosages administered to rats in the pharmacokinetics study

| Group | Test Article | Diazepam Concentration | Route of Administration | Study Dosage |
|---|---|---|---|---|
| 1 | Diastat ® - AcuDial ™ (rectal diazepam) | 5 mg/mL | Rectal | ~200 µL |
| 2 | Hospira Diazepam | 5 mg/mL | Intramuscular | ~200 µL |
| 3 | DMSO alone | 100 mg/mL | Subcutaneous | ~10 µL |
| 4 | 2% SDC in DMSO + 5% BA | 100 mg/mL | Subcutaneous | ~10 µL |
| 5 | 2% PS20 in DMSO + 5% BA | 100 mg/mL | Subcutaneous | ~10 µL |
| 6 | 10% SDS in DMSO + 5% BA | 100 mg/mL | Subcutaneous | ~10 µL |

Rat plasma samples were assayed for diazepam and nordiazepam concentrations by LC/MS using diazepam-$d_5$ and nordiazepam-$d_5$ as the internal standards. To each 25 µL sample, 25 µL of 25 ng/mL diazepam-$d_5$/nordiazepam-$d_5$ solution and 0.2 mL of water was added. The samples were vortexed, extracted using Evolute® ABN SPE plates (solid phase extraction, Biotage, Charlotte, N.C.), eluted with methanol, and dried under nitrogen at approximately 40° C. The dried residues were reconstituted in 500 µL of 1:1 methanol:water and mixed by vortexing. A reversed-phase ultra-performance liquid chromatography (RP-UPLC) and mass spectrometry (MS) method was used to measure diazepam and nordiazepam. The gradient method utilizes a chromatographic column (Waters Atlantis dC-18, 3 µm, 2.1×50 mm) with 0.1% formic acid in 60:40 (% v/v) acetonitrile:water as the mobile phase. Analyte detection was performed utilizing an ultraviolet detector at 280 nm for assay and a mass spectrometer for identity confirmation with a 0.25 mL/minute flow rate. Data obtained was expressed in ng/mL. Diazepam and nordiazepam plasma concentration data was analyzed using PKSolver Software, a menu-driven add-in program for Microsoft Excel.

Figure 2:
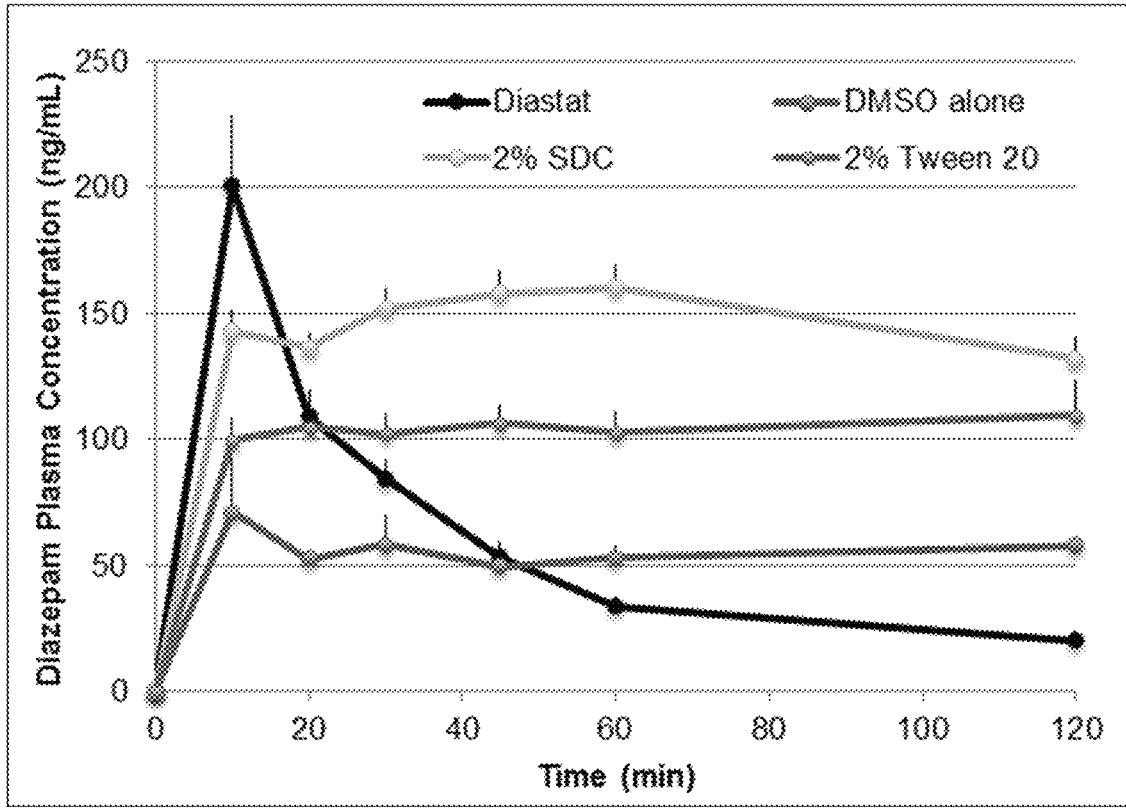
FIG. 2. Illustrates phamacokinetic profiles of diazepam in DMSO formulations compared to the Diastat® commercial formulation.

Shown in FIG. 2 are the diazepam plasma concentration profiles (mean±SEM) for Diastat® rectal diazepam, diazepam in DMSO and 5% (v/v) BA with 2% (w/v) SDC, diazepam in DMSO alone, and diazepam in DMSO and 5% (v/v) BA with 2% (v/v) PS20. The Diastat® group had a Tmax at 10 minutes with Cmax at ~200 ng/mL, and rapid decline in plasma concentration over the remaining 110 minutes. Diazepam in DMSO alone had a Tmax at 10 minutes with a Cmax of ~70 ng/mL. Unlike Diastat, diazepam in DMSO alone maintained diazepam plasma concentrations at ~50 ng/mL over the remaining 110 minutes. The lack of elimination phase observed in this group (and other DMSO groups) is believed due to partial diazepam precipitation at the injection site, followed by slow absorption. Adding 2% (v/v) PS20 to the diazepam in DMSO formulation resulted in a diazepam plasma concentration spike at 10 minutes, but due to the partial dose precipitation and slow absorption, the $T_{max}$ (110 ng/mL) occurred at 120 minutes ($C_{max}$). Adding 2% (w/v) SDC to the diazepam in DMSO formulation resulted in diazepam plasma concentration spike at 10 minutes post-injection, but with a delayed $T_{max}$ (~110 ng/mL) occurring at 60 minutes post-injection ($C_{max}$). Overall the addition of excipients to the diazepam in DMSO formulations incrementally increased the diazepam plasma concentration compared to diazepam in DMSO alone at 10 minutes post-injection.

Figure 3:
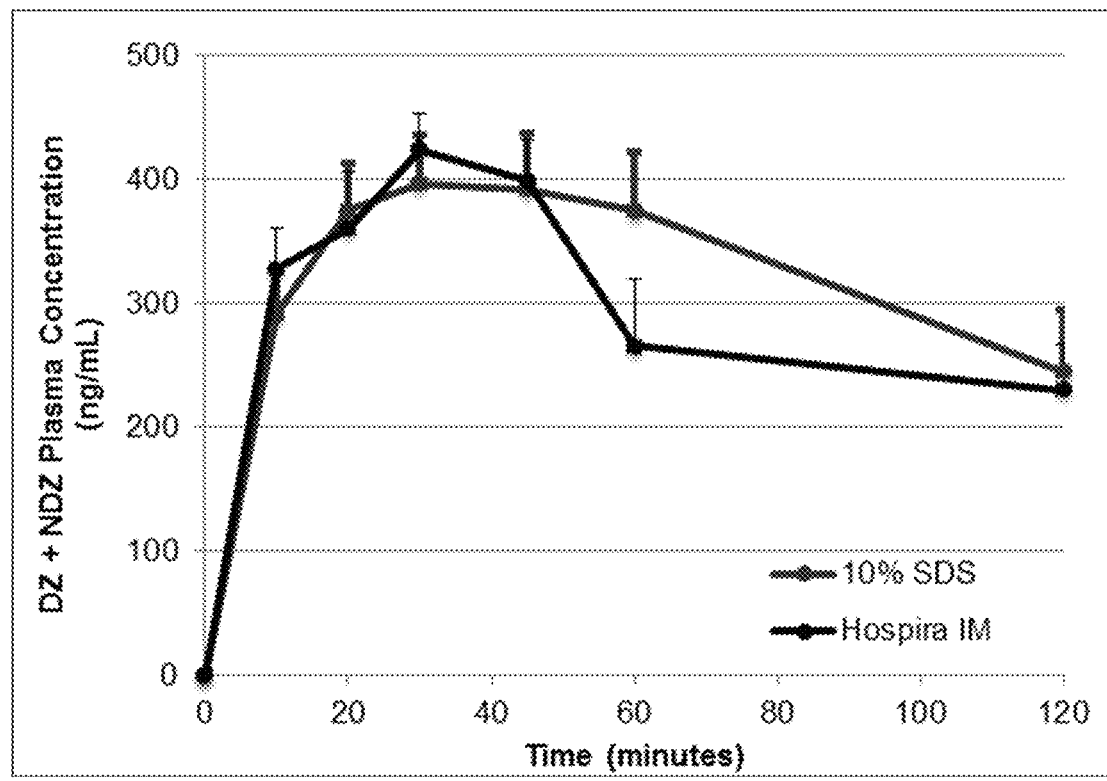
FIG. 3. Illustrates pharmacokinetic profiles of diazepam and nordiazepam in a DMSO formulation containing 10% (w/v) SDS compared to Hospira's IM formulation FIG. 4. Diazepam plasma concentrations in mini-pigs following diazepam administration.

Shown in FIG. 3 are the combined diazepam (DZ) and nordiazepam (NDZ) PK profiles (mean±SEM) of the intramuscular injection of diazepam (Hospira IM) and the diazepam in DMSO and 5% (v/v) BA with 10% (w/v) SDS formulations. Both diazepam and its metabolite, nordiazepam have pharmacodynamic activity and are clinically relevant. Both the commercial comparator and the DMSO based formulation had a $T_{max}$ at 30 minutes, and Cmax of 424 ng/mL and 396 ng/mL, respectively. The difference in $C_{max}$ between groups was statistically equivalent (p=0.3123). Together, FIG. 2 and FIG. 3 indicate that a judicious choice of excipient can modulate the diazepam PK profile, promoting either rapid or delayed/slow absorption.

Example 9

In this example the pharmacokinetic (PK) profile of diazepam in DMSO and 30% (w/v) polysorbate 80 following subcutaneous and intramuscular injection were evaluated in Gottingen mini-pig model. Studies were conducted in female mini-pigs (Xenometrics, Stilwell, Kans.) weighing between 10 and 12 kilograms, with 3 mini-pigs per group (2 groups). The animals were allowed to acclimatize for 2 weeks prior to the study. Animals were allowed a 2-week washout period between administrations. Mini-pigs were housed individually in stainless steel cages and identified numerically via a placard on the cage. Mini-pigs were observed twice-daily during the study and any abnormal health findings were recorded. Animals were fasted overnight prior to study initiation through 4 hours after dose administration.

Test articles for the PK study are described in Table 8 The study contained two commercially available diazepam formulation as comparators—Diastat® rectal (PR) diazepam (Valeant Pharmaceuticals) and Hospira's intramuscular (IM) diazepam formulation. Mini-pigs were weighted prior to study initiation to accurately administer the study dose of 1.0 mg/kg. Group 1 was dosed rectally with Diastat and group 2 received an IM injection of Hospira's diazepam in the rear thigh muscle. Group 3 received a subcutaneous dose behind the ear with the diazepam test formulation, where Group 4 received an intramuscular dose of the same formulation in the rear thigh. Animals were dosed such that the same group of animals didn't receive both intramuscular administrations. Whole blood samples were collected in vials with $K_2$ EDTA from each mini-pig via the jugular vein at time 0 (pre-dose), 0.017, 0.083, 0.167, 0.25, 0.5, 0.75, 1.0, 2.0, 4.0, 6.0, 8.0, and 24.0 hours after dose administration. Whole blood samples were centrifuged (3000 rpm, 15 minutes) and plasma was collected. Plasma samples were frozen at −70° C. for future diazepam analysis.

TABLE 8

Test articles and dosages administered to mini-pigs in the pharmacokinetic study

| Group | Test Article | Diazepam Concentration | Route of Administration | Study Dosage |
| --- | --- | --- | --- | --- |
| 1 | Diastat ® Rectal Diazepam | 5 mg/mL | Rectal | 1 mg/kg |
| 2 | Hospira Diazepam | 5 mg/mL | Intramuscular | |
| 3 | Diazepam in DMSO and 30% PS80 | 100 mg/mL | Subcutaneous | |
| 4 | Diazepam in DMSO and 30% PS80 | 100 mg/mL | Intramuscular | |

Mini-pig plasma samples were assayed for diazepam concentrations by LC/MS using diazepam-$d_5$ as the internal standard. To each 20 µL sample or standard, 500 µL of Trizma base buffer was added, followed by vortex-mixing for 1 minute. After mixing, 600 µL of ethyl acetate was added to each sample and mixed by inversion 40 times. Six hundred µL of this solution was transferred to a new collection tube and dried under nitrogen at 60° C. The dried product is reconstituted in 100 µL of reconstitution solution (1 mM ammonium formate and 0.1% formic acid in 65/35 (% v/v) methanol/water), followed by vortex-mixing for 1 minute. A reversed-phase high performance liquid chromatography (RP-HPLC) and mass spectrometry (MS) method was used to measure diazepam content. The gradient utilized a chromatographic column (Waters ACE® C18, 3 µm, 4.6×30 mm) with mobile phase A being 1 mM ammonium formate and 0.1% formic acid in 65/35 (v/v) methanol/water and mobile phase B being 1% acetic acid in 90/10 (v/v) methanol/water. Diazepam detection was performed utilizing an ultraviolet detector at 280 nm for assay and mass spectrometer for identity confirmation with a 0.25 mL/minute flow rate. Data obtained was expressed in ng/mL.

Figure 4:
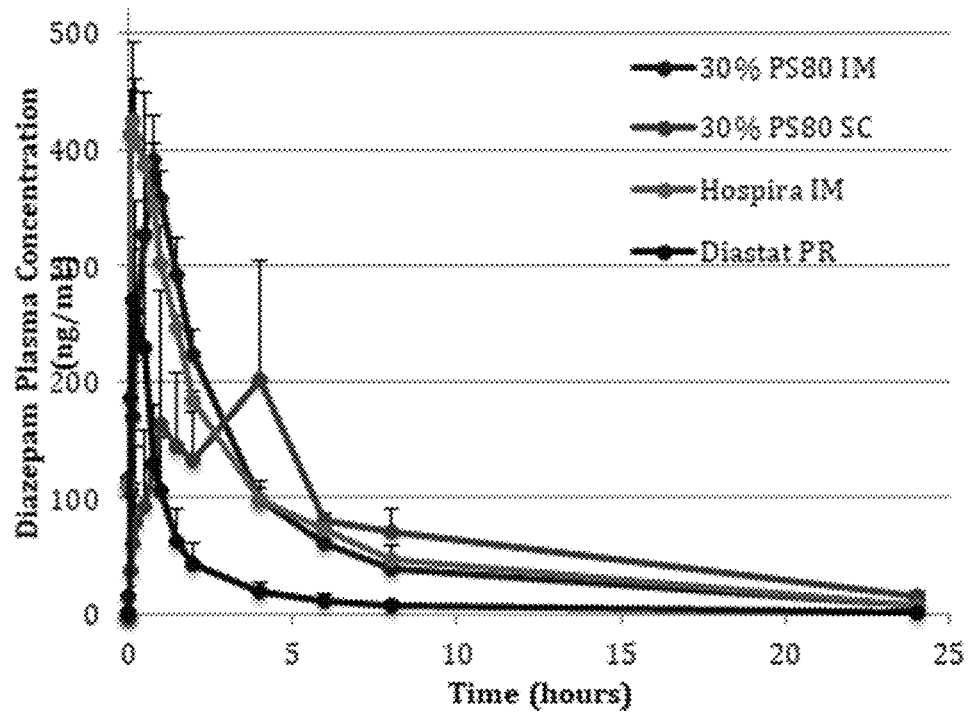

Shown in FIG. 4 are the diazepam plasma concentration profiles (mean±SEM) for 100 mg/mL diazepam in DMSO with 30% polysorbate 80 (30% (w/v) PS80) administered by intramuscular (IM) or subcutaneous (SC) injection, Hospira's diazepam administered by intramuscular injection, and Diastat® rectal diazepam. The Diastat® group had a Tmax at 10 minutes with a Cmax of ~271 ng/mL, followed by a rapid decline in plasma concentration over the first 5 hours of the study. The Hospira diazepam group also had a Tmax at 10 minutes and a Cmax of 425.3 ng/mL, followed by a rapid decline in plasma concentration, though not as rapid as Diastat rectal gel. The diazepam formulation in DMSO with 30% PS80 administered by IM injection had a Tmax at 45 minutes, Cmax of 391.3 ng/mL, and an elimination profile that matched Hospira's IM administration. The SC administration of diazepam in DMSO and 30% (w/v) PS80 resulted in three peak plasma concentrations, with a true Cmax of 202.0 ng/mL occurring at 4.0 hours. Depending on the route of administration, the pharmacokinetic profile and peak plasma concentrations of diazepam in DMSO with 30% (w/v) polysorbate 80 can have a rapid onset or prolonged systemic circulation.

Example 10

Figure 5:
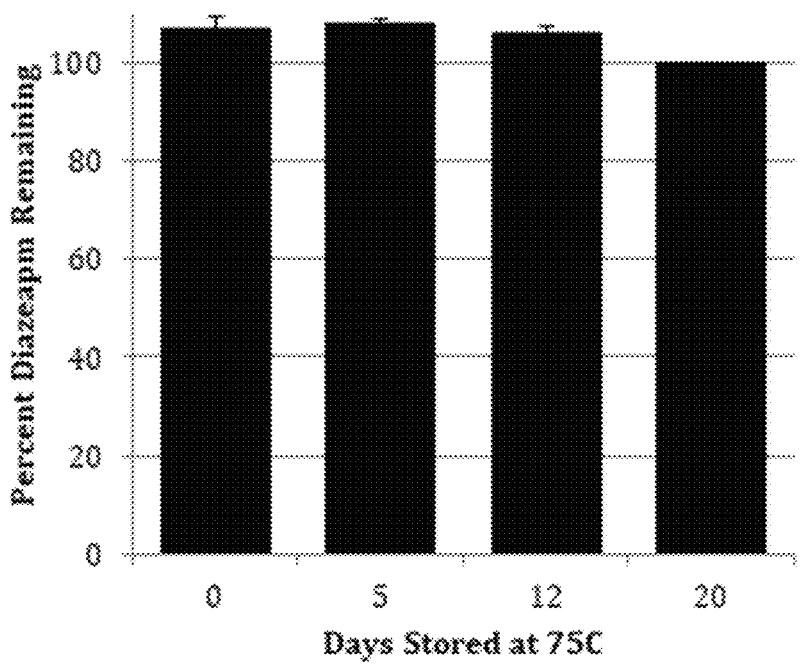
FIG. 5. Percent-diazepam remaining after 20 days storage at 75° C.

The stability of diazepam in DMSO with 30% (w/v) polysorbate 80 was studied when stored in glass vials at 75° C. for 20 days. Diazepam (100 mg/mL) was dissolved into DMSO containing 30% (w/v) polysorbate 80 and sealed into 10 mL borosilicate glass vials with 20 mm FluroTec™ stoppers and 20 mm flip-off seals. Vials were stored at 75° C. and three vials were pulled on days 5, 12, and 20. Percent-diazepam remaining in each vial was determined by RP-HPLC. Data in FIG. 5 shows the percent diazepam remaining ±standard deviation.

After 5 and 12 days of storage at 75° C. the percent-diazepam remaining was not significantly different from the initial (time zero) measurement (p=0.431). However, after 8 additional days of storage at 75° C. (day 20), the percent diazepam decreased by approximately 6.5% (106.98% to 99.99%, p=0.001). Despite the reduction in the percent-diazepam remaining after storage at 75° C., the results indicate diazepam at 100 mg/mL is stable in DMSO with 30% polysorbate 80 (w/v).

Example 11

Figure 6:
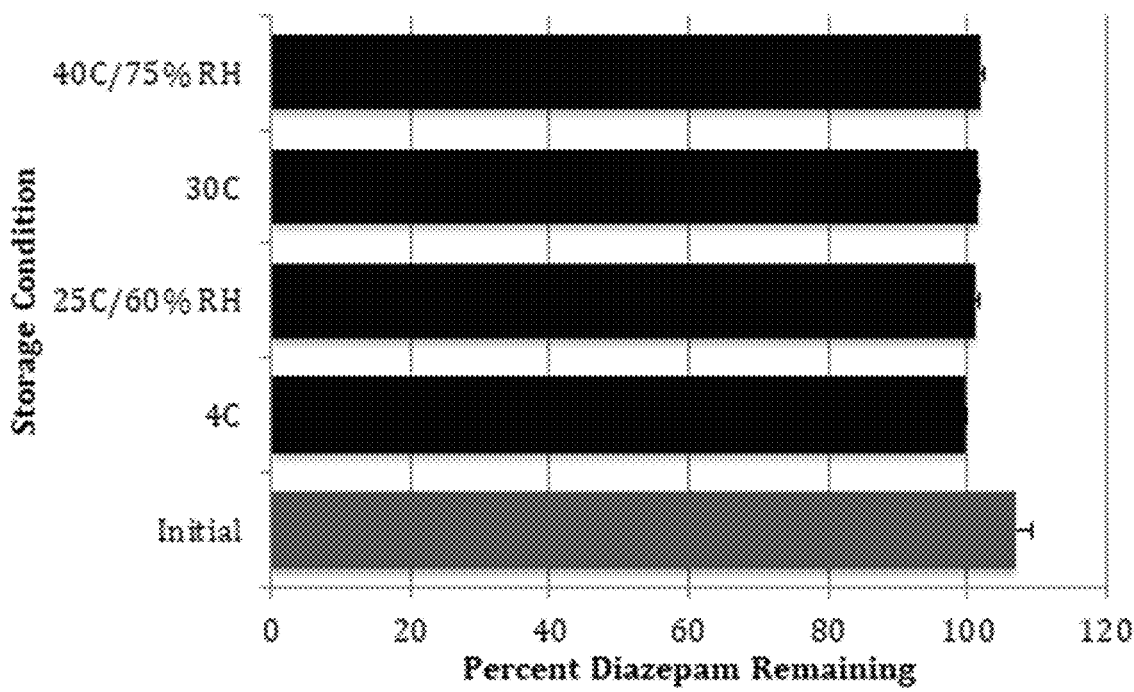
FIG. 6. Percent-diazepam remaining after 30 days of storage under different storage conditions.

The stability of diazepam in DMSO with 30% (w/v) polysorbate 80 was studied when stored in glass vials at 4-8° C., 25° C. and 60% relative humidity, 30° C., and 40° C. and 75% relative humidity. Diazepam (100 mg/mL) was dissolved in DMSO containing 30% (w/v) polysorbate 80 and sealed in 10 mL borosilicate glass vials with 20 mm Fluro-Tec™ stoppers and 20 mm flip-off seals. Vials were stored under the aforementioned storage conditions in triplicate. Percent-diazepam remaining in each vial was determined by RP-HPLC following 30 days of storage. Data in FIG. 6 shows the percent-diazepam remaining ±standard deviation.

Initial diazepam content was measure by RP-HPLC at time zero and is represented in the graph by the bottom bar labeled "Initial". The percent-diazepam remaining at any storage condition (4-8° C., 25° C./60% RH, 30° C., and 40° C./75% RH) was at 100%, showing no loss of diazepam after 30 days of storage.

The invention claimed is:

1. A stable precipitation resistant formulation for parenteral injection comprising:
 (a) a biocompatible non-aqueous aprotic solvent selected from dimethylsulfoxide (DMSO), dimethylformamide (DMF), ethyl acetate, n-methyl pyrrolidone (NMP), dimethyl acetamide (DMA), propylene carbonate, or mixtures thereof;
 (b) benzodiazepine, or a salt thereof, solubilized within the non-aqueous aprotic solvent; and
 (c) 2% to 30% w/w of a surfactant selected from sodium deoxycholate, polysorbate 80, polysorbate 20, dodecyl maltoside, or sodium dodecyl sulfate, wherein the surfactant attenuates the precipitation of the benzodiazepine when injected into a subject, and wherein the surfactant is present at a molar ratio of surfactant:benzodiazepine of 0.5:1 to 4:1.

2. The formulation of claim 1, wherein the surfactant is present at a molar ratio of surfactant:benzodiazepine of 1:1 to 2:1.

3. The formulation of claim 1, wherein the formulation comprises less than 10% by weight moisture content.

4. The formulation of claim 1, wherein the volume of the formulation to be parenterally injected is 3 mL or less.

5. The formulation of claim 1, further comprised within a device for dispensing the formulation.

6. The formulation of claim 5, wherein the device is a syringe, a pen injection device, an auto-injector device, an external or implantable pump, or a perfusion bag.

7. The formulation of claim 1, wherein the aprotic polar solvent is DMSO, NMP, or a mixture thereof.

8. The formulation of claim 1, wherein the formulation includes from 0.5 mg/mL to 750 mg/mL of the benzodiazepine.

9. The formulation of claim 1, wherein the volume of the formulation to be parenterally injected is from 1 µL to 10 µL.

10. The formulation of claim 1, wherein the volume of the formulation to be parenterally injected is from 10 µL to 100 µL.

11. The formulation of claim 1, wherein the volume of the formulation to be parenterally injected is from 100 µL to 1 mL.

12. The formulation of claim 1, wherein the benzodiazepine is diazepam.

13. The formulation of claim 1, wherein the formulation comprises 25 mg/mL to 300 mg/mL of the benzodiazepine.

14. A method of administering the formulation of claim 1 to a subject in need thereof, the method comprising parenterally injecting the formulation to the subject.

15. The method of claim 14, wherein injecting is by parenteral injection or intracutaneous injection.

16. The method of claim 14, wherein the formulation is not diluted prior to administration.

17. A method for treating or preventing anxiety, muscle spasms, or seizures, the method comprising parenterally administering to a subject in need thereof a formulation of claim 1 comprising a benzodiazepine.

18. The method of claim 17, further comprising the injectable volume within a device for dispensing the formulation.

19. The method of claim 18, wherein the device is a syringe, a pen injection device, an auto-injector device, an external or implantable pump, or a perfusion bag.

20. The method of claim 17, wherein the formulation comprises 25 mg/mL to 300 mg/mL of a benzodiazepine.

21. The method of claim 17, wherein the benzodiazepine is diazepam.

22. The method of claim 17, wherein the volume of the formulation to be parenterally injected is from 1 µL to 10 µL.

* * * * *